Figure 1A:
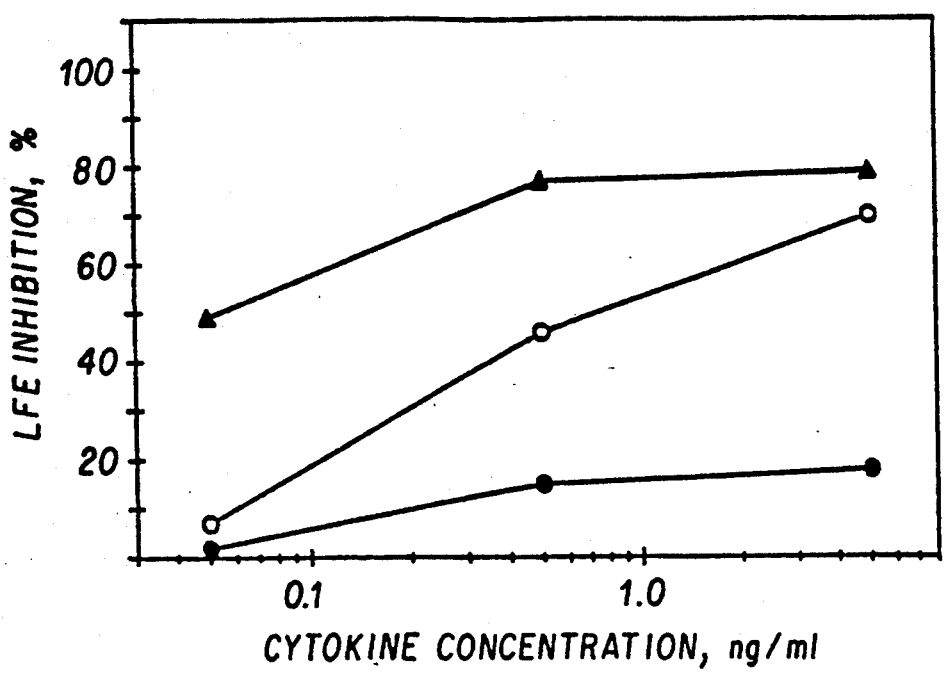

United States Patent [19]
Brown et al.

[11] Patent Number: 5,202,116
[45] Date of Patent: Apr. 13, 1993

[54] METHODS FOR CONTROLLING HUMAN ENDOTHELIAL CELL PROLIFERATION AND EFFECTOR FUNCTIONS USING ONCOSTATIN M

[75] Inventors: Thomas J. Brown, Poulsbo; Paul R. Gladstone, Seattle, both of Wash.

[73] Assignee: Oncogen, Seattle, Wash.

[21] Appl. No.: 335,399

[22] Filed: Apr. 10, 1989

[51] Int. Cl.$^5$ ............................................. A61K 45/00
[52] U.S. Cl. ..................... 424/85.1; 514/12; 424/450; 424/489; 530/402; 530/403
[58] Field of Search ................... 514/12; 424/88, 85.1, 424/85.8, 450, 489; 530/402, 403

[56] References Cited

U.S. PATENT DOCUMENTS 4,671,958  6/1987  Rodwell et al. ........................ 424/85
5,120,535  6/1992  Marquardt et al. ................. 424/85.5

FOREIGN PATENT DOCUMENTS 0290948  11/1988  European Pat. Off. .

OTHER PUBLICATIONS

J. Cell Biol. O(13 Part E):189. 1988, T. Brown, et al. Oncostatin M as unique modulator . . .
J. Biol. Chem. 264:4282-9. P. S. Linsley, et al. Mar. 15, 1989. Identification and Characteriz . . .
P.N.A.S. 83:9739-43. J. Zarling, et al. Dec. 1986. Oncostatin: A Growth Regulator . . .
J. Immunol. 139:2977-83. T. J. Brown, et al. Nov. 1987. Purification and . . .
Babany et al., 1988, J. Pharmacol. Exp. Ther. 244(1): 259-262.
Britton et al., 1982, Immunol. Rev. 65: 5-22.
Brown et al., 1988, J. Cell. Biochem. Suppl. O (12 Part A): 194.
Burton et al., Jul. Supplement 1982, J. Clin, Immunol. 2 (No. 3): 142S-147S.
Collins et al., 1984, Proc. Natl. Acad. Sci. USA 81:4917-4921. ("Collins I").
Collins et al., 1986, Proc. Natl. Acad. Sci. USA 83:446-450 ("Collins II").
Cosimi et al., 1981, Transplantation 32 (No. 6): 535-539 ("Cosimi I").
Cosimi et al., 1981, New Eng. J. Med. 305: 308-314. ("Cosimi II").
Czarniecki et al., 1988, J. Immunol. 140 (No. 12): 4217-4223.
de Waal et al., 1983, Nature 303: 426-429.
Embleton et al., 1985, "Monoclonal Antibodies For Cancer Detection and Therapy", Baldwin, R. W. et al. eds., Academic Press London, pp. 317-344.
Feldman et al., 1987, Interferon 9: 75-90.
Ferry et al., 1987, Transplantation 44 (No. 4): 499-503.
Fung et al., 1986, Human Immunol. 16:182-199.
Geppert et al., 1985, J. Immunol. 135 (No. 6): 3750-3762.
Ghose et al., 1983, Meth. Enzymol. 93: 280-333.
Giorgi et al., 1983, Diagnostic Immunol. 1: 174-178.
Goldstein, 1987, Transplant. Proc. 19 (No. 2), Suppl. 1:1-6.
Gunderson et al., 1988, J. Cell. Biochem. Suply. O (12Part A):224.
Hardy, 1986, "Handbook of Experimental Immunology, Vol. 1: Immunochemistry", Weir, D. M. et al. eds., Blackwell Scientific Publications, pp. 31.1-31.12.

(List continued on next page.)

Primary Examiner—Christine M. Nucker
Assistant Examiner—T. Cunningham
Attorney, Agent, or Firm—Pennie & Edmonds

[57] ABSTRACT

The present invention is directed to the use of a recently discovered cytokine, Oncostatin M, to control endothelial cell immunogenicity, fibrinolytic activity and proliferation, and to its use in the treatment of a variety of human vascular and immune system disorders involving the vascular endothelium. The method of the invention includes the use of mature, hybrid, modified or truncated forms of Oncostatin M as well as Oncostatin M analogs. The invention is described by way of examples in which the efficacy of such compounds is evaluated using various in vitro assay systems.

10 Claims, 13 Drawing Sheets

OTHER PUBLICATIONS

Hirsch et al., 1987, Transplant. Proc. 19 (No. 2),Suppl. 1:32-36.

Hurwitz et al., 1975, Canc. Res. 35: 1175-1181.

Jacobs et al., 1986, J. Interferon Res. 6 (suppl. 1): 37.

Kadin et al., 1982, "Antibody As A Tool", Marchalonis, J. J. ed., John Wiley & Sons NY, pp. 447-484.

Lapierre et al, 1988, J. Exp. Med. 167: 794-804.

Linsley et al., 1988, J. Cell. Biochem. Suppl. O (12 Part A): 227.

Matis et al., 1983, Proc. Natl. Acad. Sci. USA 80: 6019-6023.

May et al., 1986, Proc. Natl. Acad. Sci. USA 83: 8957-8961.

Milton et al., 1985, J. Exp. Med. 161: 98-112.

Obert, 1986, J. Interferon Res. 6 (suppl. 1): 37.

Pietersz et al., 1988, "Antibody-Mediated Delivery Systems", Rodwell, J. D. ed., Marcel Dekker, Inc. NY, pp 25-53.

Pober et al, 1983, Nature 305: 726-729. ("Pober 1").

Pober et al, 1987, J. Immunol. 138 (No. 10): 3319-3324.

Revel et al., 1987, "Autoimmunity and Autoimmune Disease", Wiley, Chichester, pp. 223-233.

Senter et al, 1988, Proc. Natl. Acad. Sci. USA 85: 4842-4846.

Shimizu et al., 1980, FEBS Letters 118 (No. 2): 274-278.

Takahashi et al., 1987, Transplant. Proc. 19 (No. 1): 794-799.

Vigeral et al., 1985, "Monoclonal Antibodies: Diagnostic And Therapeutic Use in Tumor and Transplantation", Chatterjee, S. N. ed., PSG Publishing MA, pp. 79-83. ("Vigeral 1").

Vigeral et al., 1986, Transplantation 41 (No. 6): 730-733.("Vigeral II").

Wallis et al., 1986, Pathol. Immunopathol. Res. 5: 73-103.

Zeevi et al., 1986, Transplantation 41 (No. 5): 620-626.

FIG. 10A
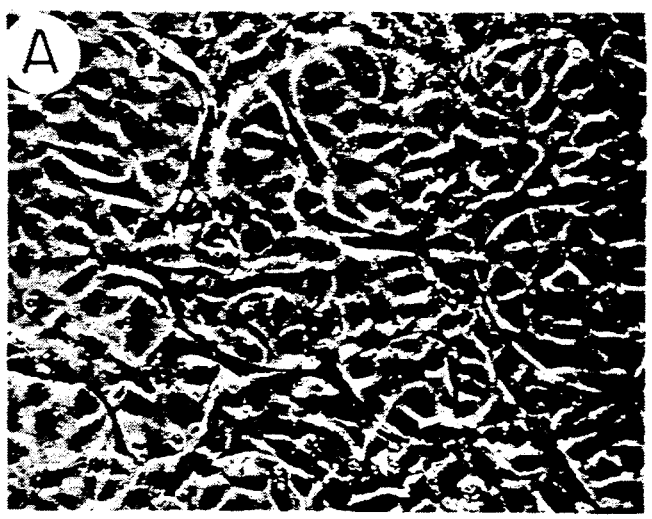
FIG. 10B

METHODS FOR CONTROLLING HUMAN ENDOTHELIAL CELL PROLIFERATION AND EFFECTOR FUNCTIONS USING ONCOSTATIN M

TABLE OF CONTENTS

1. Introduction
2. Background of the Invention
    2.1. Expression of Major Histocompatibility Complex Antigens and Relationship to Immune Response
        2.1.2. Endothelial Cell Expression of MHC Antigents: Relationship to Allograft Rejection
    2.2. Role of Endothelium in Fibrinolysis and Thrombosis
    2.3. Antiogenesis
3. Summary of the Invention
4. Description of the Figures
5. Detailed Description of the Invention
    5.1. Oncostatin M as an Immunomodulator
        5.1.1. Use of Oncostatin M in Organ Transplantation
    5.2. Use of Oncostatin M to Induce a Fibrinolytic Phenotype in Vascular Endothelium
    5.3. Use of Oncostatin M to Control Angiogenesis
6. Example: Modulation of Endothelial Cell HLA Antigen Expression by Oncostatin M in vitro
    6.1. Materials and Methods
        6.1.1. Endothelial cell cultures
        6.1.2. Immunostaining
        6.1.3. Quantitative Antigen Assay
        6.1.4. Cytokines
        6.1.5. Oncostatin M Receptor Assay
    6.2. Results
        6.2.1. Oncostatin M Inhibits Cytokine-Stimulated HLA Expression on Human Endothelial Cells
        6.2.2. Synergistic Action of Oncostatin M and TGF-$\beta$
        6.2.3. Tissue Specificity of Oncostatin M Effect on HLA Expression
        6.2.4. High Level Expression of Oncostatin M Receptors on HUVECs
7. Example: Induction of Fibrinolytic Activity in Aortic Endothelial Cells by Oncostatin M
    7.1. Materials and Methods
        7.1.1. Cell Culture
        7.1.2. Plasminogen Activator Activity Assay
        7.1.3. Oncostatin M Receptor Assay
    7.2. Results
        7.2.1. Specific Stimulation of Plasminogen Activator Activity by Oncostatin M
        7.2.2. BAEC Cell-Surface Receptors For Oncostatin M
8. Example: Antiproliferative Effects of Oncostatin M on Endothelial Cells
    8.1. Growth Inhibition Assays
    8.2. Monocyte Chemotaxis Assay
    8.3. Results
9. Example: Characterization of Morphological Changes Induced by Oncostatin M on Endothelial Cells
    9.1. Cell Culture
    9.2. Leukocyte Adherence Assay
    9.3. Oncostatin M Induces Morphological Changes in BAECs

1. INTRODUCTION

The present invention is directed to the use of a recently discovered cytokine, Oncostatin M, for controlling human endothelial cell proliferation and effector functions, and to its use in the treatment of a variety of human vascular and immune system disorders involving the vascular endothelium. The method of the invention includes the use of mature, hybrid, modified or truncated forms of Oncostatin M as well as Oncostatin M analogs. The invention is described by way of examples in which the efficacy of such compounds is evaluated using various in vitro assay systems.

2. BACKGROUND OF THE INVENTION

2.1. Expression of Major Histocompatibility Complex Antigens and Relationship to Immune Response Surface-expressed proteins of the major histocompatibility complex (MHC) are integral for the initiation and effector functions of immune responses. Initiation of immune functions by CD4+T cells (helpers) appears to require class II MHC antigen presentation, while cytotoxic effector functions by CD8+T cells (cytotoxic T lymphocytes or CTLs) appear to require class I MHC antigen presentation. It is known that cell surface expression of MHC proteins correlates with human autoimmune and alloimmune diseases (reviewed in Feldman et al., in *Interferon* 9: 75-90, Academic Press 1987). Tissue cells in the majority of human autoimmune diseases including, for example, thyroiditis, diabetes, multiple sclerosis, systemic lupus erythematosus, rheumatoid arthritis, Sjogren's syndrome, vasculitis, biliary cirrhosis and immunologically-related skin disorders, as well as alloimmune diseases such as graft vs. host disease, express abnormally elevated levels of class I and class II MHC antigens. When cells that ordinarily do not express class II antigens (e.g., fibroblasts and endothelial cells) begin to express this class of antigen, they become immunoreactive targets for lysis and destruction by CTLs (Pober et al., 1983, Nature 305: 726).

MHC antigen expression on many cell types is largely under the regulatory control of various cytokines. Cells such as macrophages, dermal fibroblasts, keratinocytes, thyrocytes, astrocytes, B islet cells, smooth muscle cells, T lymphocytes, endothelial cells and many cancer cells, require induction by cytokines for class II MHC antigen expression (Revel and Schattner, in *Autoimmunity and Autoimmune Disease* 223-233, Wiley 1987). Members of the interferon family are primarily involved with the upregulation of MHC expression and all types of interferons appear to enhance class I expression, although IFN-$\gamma$ is the best studied and most potent in this regard. In addition, the cytotoxins known as tumor necrosis factors (TNF-$\alpha$ and TNF-$\beta$) have demonstrated the ability to enhance class I expression in fibroblasts via induction of IFN-$\beta$2 (May et al., 1987, Proc. Natl. Acad Sci. USA 83: 8957). While the induction of class II antigens by IFN-$\alpha$ and IFN-$\beta$ is usually not significant, IFN-$\gamma$ is a potent inducer of class II molecules at the gene level (Collins et al., 1984, Proc. Natl. Acad. Sci. USA 81: 4917). Some cytokines appear to synergize with IFN-$\gamma$ in the induction of MHC antigen expression; for example, TNF-$\alpha$ and TNF-$\beta$ act synergistically with IFN-$\gamma$ on expression of class I antigens on endothelial cells without affecting IFN-$\gamma$-mediated induction of class II antigens (Lapierre et al., 1988, J. Exp. Med. 167: 794).

The level of MHC antigen expression on a cell's surface is a determinant of its antigen-presenting capacity (Matis et al., 1983, Proc. Natl. Acad. Sci. USA 80: 6090). Therefore, compounds that interfere with or antagonize over-expression of MHC antigens beyond immunologically-tolerated thresholds may have therapeutic utility in, for example, slowing or stopping the progression of autoimmune diseases. In the case of transplanted organs, the expression level of the donor MHC antigens is an important determinant of the severity of the rejection response (Ferry et al., 1987, Transplantation 44: 499). Transforming Growth Factor-$\beta$ (TGF-$\beta$) has been shown to inhibit the level of class II expression induced by IFN-$\gamma$ on human melanoma cells and peripheral blood mononuclear cells without affecting class I expression (Czarniecki et al., 1988, J. Immunol. 140: 4217).

2.1.2. Endothelial Cell Expression of MHC Antigens: Relationship to Allograft Refection Vascular endothelial cells play a central role in the process of allograft rejection. Immunohistologic studies of tissue rejection have demonstrated that vascular endothelial cells from MHC-incompatible heart or skin express high levels of class II MHC antigens early in the rejection process (De Waal et al., 19883, Nature 303: 426–429; Milton and Fabre, 1985, J. Exp. Med. 161: 98–112). In its inception, immunologic rejection of allotransplantations involves the interaction between recipient T cells and the donor organ vasculature; other cells become involved as rejection progresses. In organ transplants the endothelium is the donor tissue which is the first target of attack by host T cells recognizing donor HLA antigens on the surface of endothelial cells. T cell infiltration through the vascular endothelium has been described as a four step process: recognition, adherence, activation, and penetration of alloactivated T cells through the vascular wall (Fung et al.,1986, Human Immunol. 16: 182). Activated T cells produce gamma-Interferon (IFN-$\gamma$) and Tumor Necrosis Factor (TNF) which stimulate the expression of class II HLA antigens on the surface of the donor endothelium, thereby transforming the donor endothelium to a more immunogenic state. Increased expression of class I antigens also results from induction by gamma-IFN and TNFs, probably augmenting the target function of the endothelium in interactions with cytotoxic T lymphocytes. In early biopsies of rejected kidney grafts, T cells with a specificity for class I HLA antigens are predominant; as rejection progresses, T cells specific for class II HLA antigens are prevalent (Zeevi et al., 1986, Transplantation 41: 620). Similar results have been found in heart transplants. The degree of alloimmune response and, ultimately, rejection depends on the expression of both class I and class II HLA molecules, and even small reductions in their expression levels leads to substantially improved outcomes.

Endothelial cells provide a good model for studying cytokine regulation of MHC expression in vitro since these cells are readily available from primary tissue and are known to function as antigen presenting cells following treatment with cytokines. Cultured human umbilical endothelial cells (HUVECs) constitutively express class I but not class II MHC (HLA) antigens under normal culture conditions. Alpha and beta interferons (IFN-$\alpha$, IFN-$\beta$), as well as alpha and beta tumor necrosis factors (TNF-$\alpha$, TNF-$\beta$), increase the levels of class I HLA expression in HUVECs without affecting class II HLA levels (Collins et al., 1986, Proc. Natl. Acad. Sci. USA 38: 446; Pober et al., 1987, J. Immunol. 138: 3319). Only gamma interferon(IFN-$\gamma$) demonstrates the capacity to upregulate both class I and II HLA expression (Geppert and Lipsky, 1985, J. Immunol. 135:3750). Cytokine treatment of HUVECs results in increased levels of steady-state RNA levels for HLA antigens as well as increased cell-surface expression (Collins et al., 1986, Proc. Natl. Acad. Sci. USA 38: 446). TNF-$\alpha$ and TNF-$\beta$ act synergistically with IFN-$\gamma$ to enhance class I MHC expression without affecting IFN-$\gamma$-mediated class II induction (Lapierre et al., 1988, J. Exp. Med. 167: 794). In contrast, neither IFN-$\gamma$ nor IFN-$\beta$ synergize with IFN-$\gamma$ to enhance class I expression, but both inhibit the IFN-$\gamma$-mediated induction of class II expression.

2.2. Role of Endothelium in Fibrinolysis and Thrombosis

Hemostasis of the vascular system is a function of the interactions between blood vessels, the formed elements of blood such as monocytes and platelets, and various blood coagulation proteins. Abnormalities in coagulation proteins can result in hemmorragic and thrombolytic disorders. Thrombosis is a primary component in the pathogenesis of, for example, artherosclerosis and coronary heart disease (Gadjusek et al., 1986, J. Cell Biol. 103: 419).

Dissolution of thrombi depends critically on the degradation of the clot component fibrin by the serine protease plasmin. Plasmin is generated from its inactive precursor, plasminogen, by two plasminogen activators: tissue-type plasminogen activator (t-PA) and urokinase-type plasminogen activator (u-PA). Vascular endothelial cells line the luminal surface of the vascular bed and secrete both t-PA and u-PA, as well as multiple molecular forms thereof (Booyse et al., 1988, J. Biol. Chem. 263: 15129), and are believed to be actively involved in the specific breakdown of locally deposited fibrin.

Plasminogen activators, plasminogen and plasmin all bind to fibrin molecules. Interestingly, t-PA but not u-PA requires fibrin as a cofactor for maximal catalytic efficiency, suggesting that a major physiologic function of t-PA may be the modulation of endothelial cell-mediated fibrinolysis (Camiolo et al., 1971, Proc. Soc. Exp. Biol. Med. 138: 2771). Localization of fibrinolysis to the fibrin clot is further controlled by PA inhibitors (PAIs). PAI-1, the primary inhibitor found in plasma and serum, inactivates t-PA and u-PA by forming one to one complexes and plays an important role in regulating fibrinolysis (van Mourik et al., 1984, J. Biol. Chem. 259: 14914). Thus, the level of endothelial cell-mediated fibrinolytic activity expressed extracellularly represents the net balance between PAs and PAI-1.

The synthesis and release of both PA and PAI-1 by endothelial cells is regulated to some degree by hormones and cytokines. Basic fibroblast growth factor (bFGF) stimulates the expression Of u-PA and t-PA in bovine capillary endothelial cells (Saksela et al., 1987, J. Cell Biol. 105: 957), an effect antagonized by transforming growth factor-$\beta$ (TGF-$\beta$) which inhibits PA synthesis while promoting the synthesis and secretion of PAI-1 (Laiho et al., 1987, J. Biol. Chem. 262: 17467; Saksela et al., 1987, J. Cell Biol. 105: 957). The inflammatory cytokines TNF-$\alpha$ and IL-1 have also been characterized as fibrinolytic inhibitors since they amplify the synthesis and secretion of PAI-1 (Nachman et al., 1986, J. Exp. Med. 163: 1545).

Evidence from in vitro studies show that the endothelium plays an active role in regulating thrombotic processes. Endothelium maintains an anti-thrombolytic phenotype under normal conditions and inhibits thrombus formation in vivo by four known mechanisms: inactivating thrombin, inhibiting thrombin expression, inhibiting platelet adhesion and aggregation, and fibrinolysis (reviewed in Wallis and Harlan, 1986, Pathol. Immunopathol. Res. 5: 73-103). Three thrombolytic agents are currently in widespread use: streptokinase, urokinase and recombinant t-PA. These agents convert circulating plasminogen to plasmin, which in turn lyses the fibrin component in thrombi. Although t-PA has certain advantages in that its action is directed to fibrin clots since it requires fibrin as a cofactor, like streptokinase and urokinase it can also solubilize hemostatic plugs where they are needed most. In the short time that it has been available to patients suffering from acute myocardial infarction, t-PA has demonstrated deleterious side effects including systemic hemorrhagic complications. Therefore, more specific and controllable means for enhancing thrombolysis is desirable.

2.3 Antiogenesis

Angiogenesis, or neovascularization, is the process of new blood vessel formation by endothelial cells and is rare in adults under normal physiological conditions except during wound repair, ovulation, menstruation and placenta formation. The balance between naturally occurring inducers and inhibitors of angiogenesis usually resolves in favor of inhibitory influences. Angiogenesis is often associated with disease, such as diabetic retinopathy, neovascular glaucome, rheumatoid arthritis, hemangioma and cancer (Folkman, in *Thrombosis and Hemostasis* 583-596, Verstraete et al., Eds., Leuven University Press 1987). Tumors produce a variety of factors which activate and attract endothelial cells (Folkman and Klagsbrun, 1987, Science 235: 442) and the vigorous angiogenesis that results is absolutely necessary for their continued growth and metastases (Folkman and Cotran, 1976, Int. Rev. Exp. Pathol. 16: 207).

Another form of life-threatening disease associated with angiogenesis is Kaposi's sarcoma (KS) which develops in patients suffering from infection with the human immunodeficiency virus type 1 (Friedman-Kein et al., 1982, Ann. Int. Med. 96: 693) and in patients receiving immunosuppressive therapy (Greenfield et al., 1986, J. Rhematol. 13: 637). KS lesions are characterized by a highly vascularized hemorrhagic histological pattern. The tumor is believed to be of endothelial origin (Macher, 1988, Public Health Report 103: 246). KS cells isolated from patients with Acquired Immune Deficiency Disease (AIDS) produced strong angiogenic reactions in mice, resulting in characteristic KS lesions (Salahuddin et al., 1988, Science 242: 430). KS cells also secrete factors which have mitogenic effects on cultured endothelial cells. The therapeutic benefit of compounds which control pathologic angiogenesis in such diseases has led to a search for effective inhibitors of neovascularization.

A number of compounds which inhibit neovascularization have been identified such as anti-inflammatory agents (Polverini and Novak, 1986, Biochem. Biophys. Res. Comm. 140: 90), angiostatic steroids (Ingber et al., 1986, Endocrinol. 119: 1768), placental RNAse inhibitor (Shapiro and Vallee, 1987, Proc. Natl. Acad. Sci. USA 84: 2238), as well as a variety of compounds which influence matrix synthesis and integrity (Ingber and Folkman, 1988, Lab. Invest. 59: 44). Certain cytokines also demonstrate angiostatic activities including IFN-$\gamma$, TNF-$\alpha$ and TGF-$\beta$, all of which have been shown to block the proliferative response of cultured endothelial cells to basic fibroblast growth factor (bFGF), a potent angiogenic promoter (Bolen et al., in *Current Comminications in Molecular Biology*, 119-124, Rifkin and Klagsbrun, Eds., Cold Spring Harbor Press 1987). However, when these cytokines were tested in rabbit corneal neovascularization assays, they exhibited angiogenic activity, a response thought to result from the chemotactic effects of these cytokines on inflammatory leukocytes involved in the release of angiogenic factors (Freter-Schroder et al., 1987, Proc. Natl. Acad. Sci. USA 84: 527). Another cytokine, interleukin-1 (IL-1) also demonstrates angiogenic properties in the rabbit eye anterior chamber model initiating inflammatory response as well as leukocyte infiltration (Dinarello, 1989, in *Advances in Immunology* 44:153, Academic Press).

Tumor-induced angiogenesis can be demonstrated by placing malignant tumor tissue into the rabbit cornea in which vaso-proliferation originates from the limbal vessels and migrates towards the tumor graft. Chakravarti and Maitra found that vaso-proliferation could be inhibited in this model by placing a piece of mesenteric lymph node containing activated lymphocytes along with the tumor graft (Chakravarti and Maitra, 1983, Experientia 39: 542). It is possible that Oncostatin M, a natural product of T cells, is involved in the inhibition observed in that study.

3. SUMMARY OF THE INVENTION

The use of Oncostatin M to control endothelial cell immunogenicity, fibrinolytic activity and proliferation is described. Oncostatin M purified from natural sources, recombinant Oncostatin M, or Oncostatin M prepared by chemical synthetic techniques may be used. The invention is described by way of examples in which the various effects of Oncostatin M on several cell types are determined using in vitro assays.

The invention is subdivided for the purpose of description according to the different areas of therapeutic utility it encompasses. First, the invention is directed to the use of Oncostatin M to mitigate endothelial tissue immunogenicity, the primary element involved in the rejection of allografted organs and the progression of certain autoimmune diseases. This aspect of the invention is described by way of examples in which the ability of Oncostatin M to inhibit the expression of MHC antigens on the surface of human endothelial cells in vitro is demonstrated. Oncostatin M is capable of substantially antagonizing IFN-$\gamma$ and TNF-$\alpha$ stimulated expression of class I and class II HLA antigens and appears to be specific for action on endothelial cells. Second, the invention is directed to the use of Oncostatin M to induce and/or maintain the fibrinolytic phenotype in vascular endothelium, a state of affairs vital to sustaining normal functioning of the vascular system. This aspect of the invention is described by way of examples in which the ability of Oncostatin M to stimulate vascular endothelial cell plasminogen activator activity, resulting in increased levels of bioactive plasmin, is demonstrated. Applicants show that Oncostatin M specifically induces the expression of active plasminogen activator molecules and/or inhibits the expression and/or function of plasminogen activator inhibitors. Third, the invention is directed to the use of Oncostatin M to inhibit the process of angiogenesis, a prominent component in the pathology of many life-threatening diseases including cancer. This aspect of the invention is described by way of examples in which the ability of Oncostatin M to inhibit endothelial cell proliferation in response to mitogenic stimulation by angiogenic factors is demonstrated. The effects of Oncostatin M on endothelial cell morphology and chemotaxis are also described.

4. DESCRIPTION OF THE FIGURES

Figure 1B:
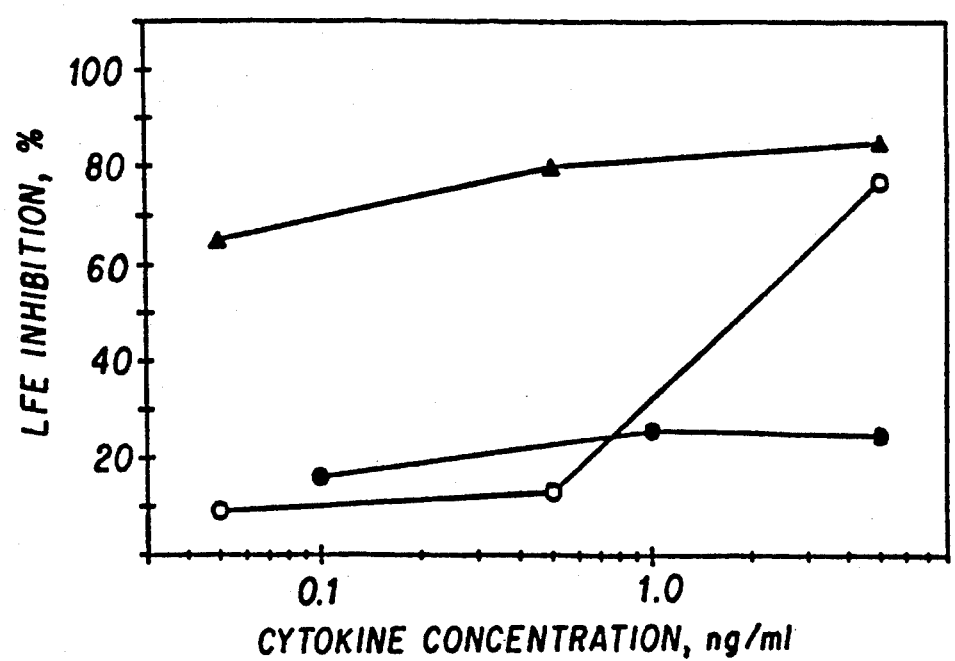

FIGS. 1A and 1B. Synergistic inhibitory effects of Oncostatin M and TGF-$\beta$ on endothelial cell HLA antigen expression induced by IFN-$\gamma$. Oncostatin M (○); TGF-$\beta$ (●); Oncostatin M plus TGF-$\beta$ (▲). FIG. 1A Effects on class I HLA antigen expression. FIG. 1B Effects on class II HLA-DR antigen expression.

Figure 2A:
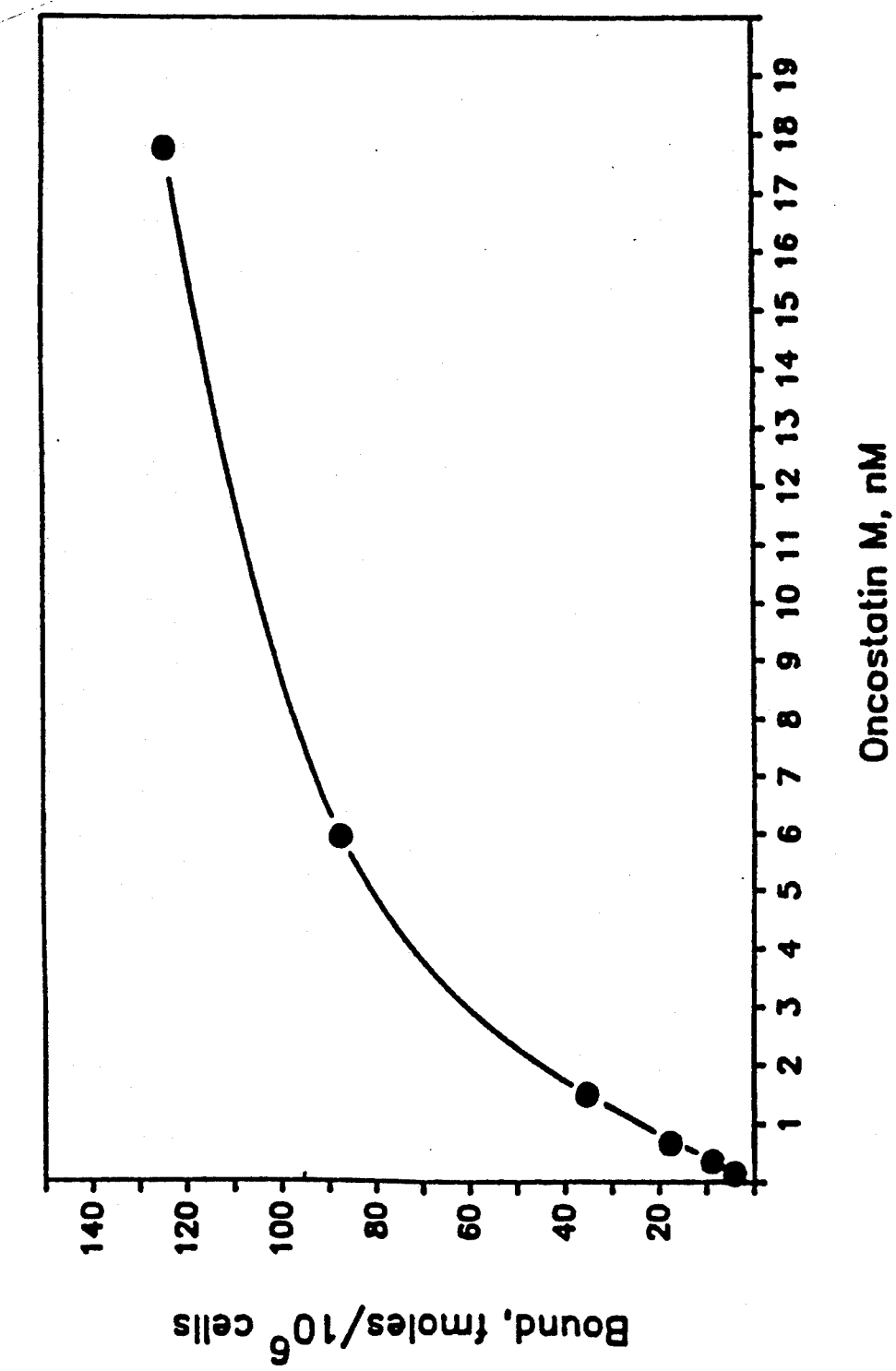
Figure 2B:
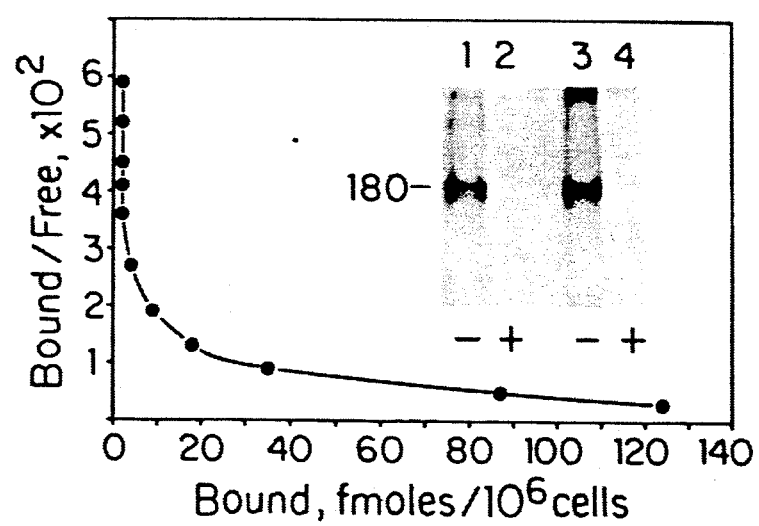

FIGS. 2A and 2B Oncostatin M receptor binding on HUVECs: FIG. 2A depicts a saturation curve and FIG. 2B depicts a scratched plot and SDS-PAGE autoradiograph (inset). Data obtained and compiled as described in Section 6.2.4., infra.

Figure 3:
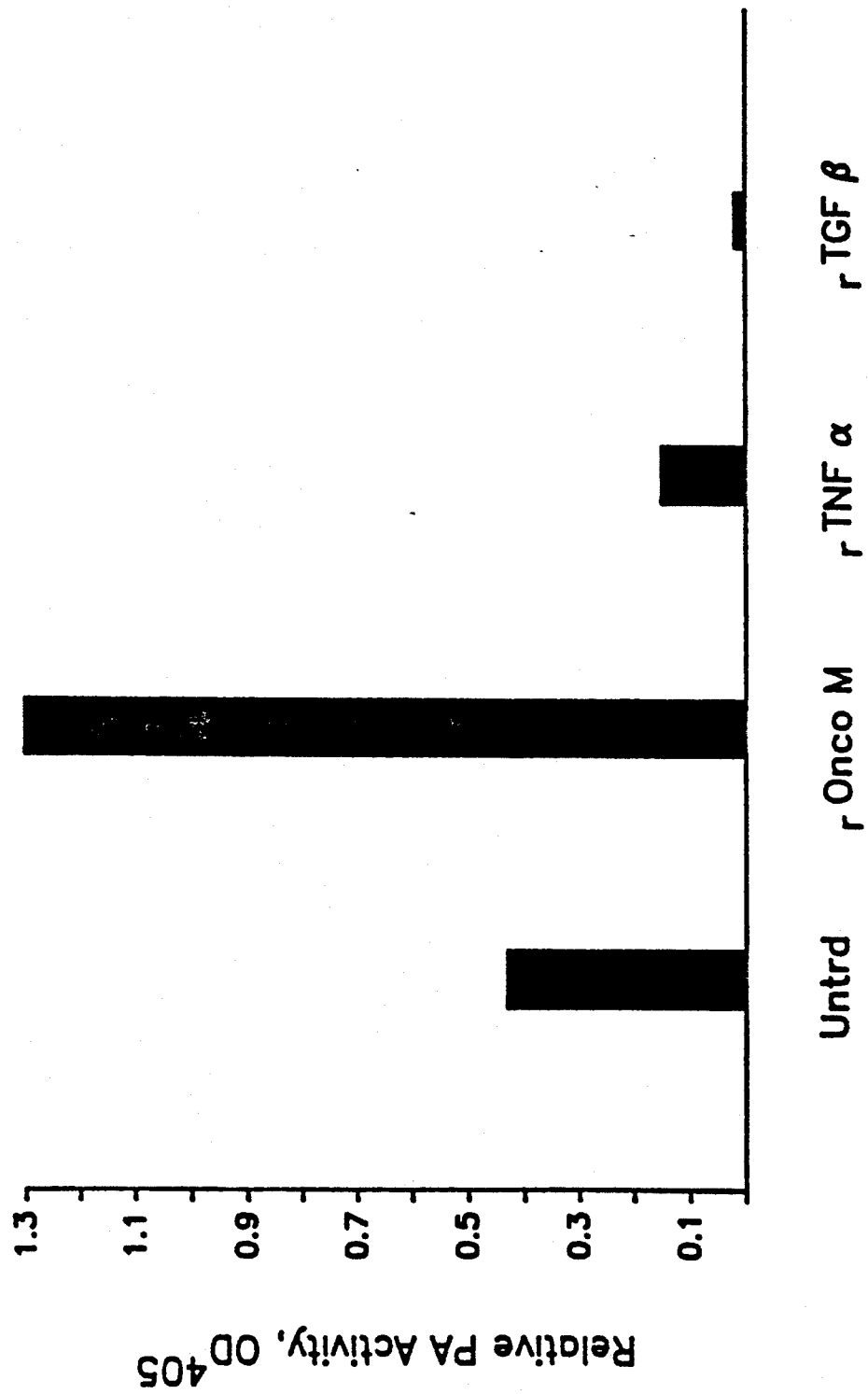

FIG. 3. Specificity of Oncostatin M action for induction of PA activity on endothelial cells. BAECs were treated for 72 hours with 10 nM recombinant Oncostatin M (Malik et al., 1989, Mol. Cell. Biol., in press), recombinant TNF-$\alpha$ (AmGen) and recombinant TGF-$\beta$ (Gentry et al., 1987, Mol. Cell. Biol. 7: 3418-3427). Cell-associated PA activity was determined as described in Section 7.1.2., infra.

Figure 4A:
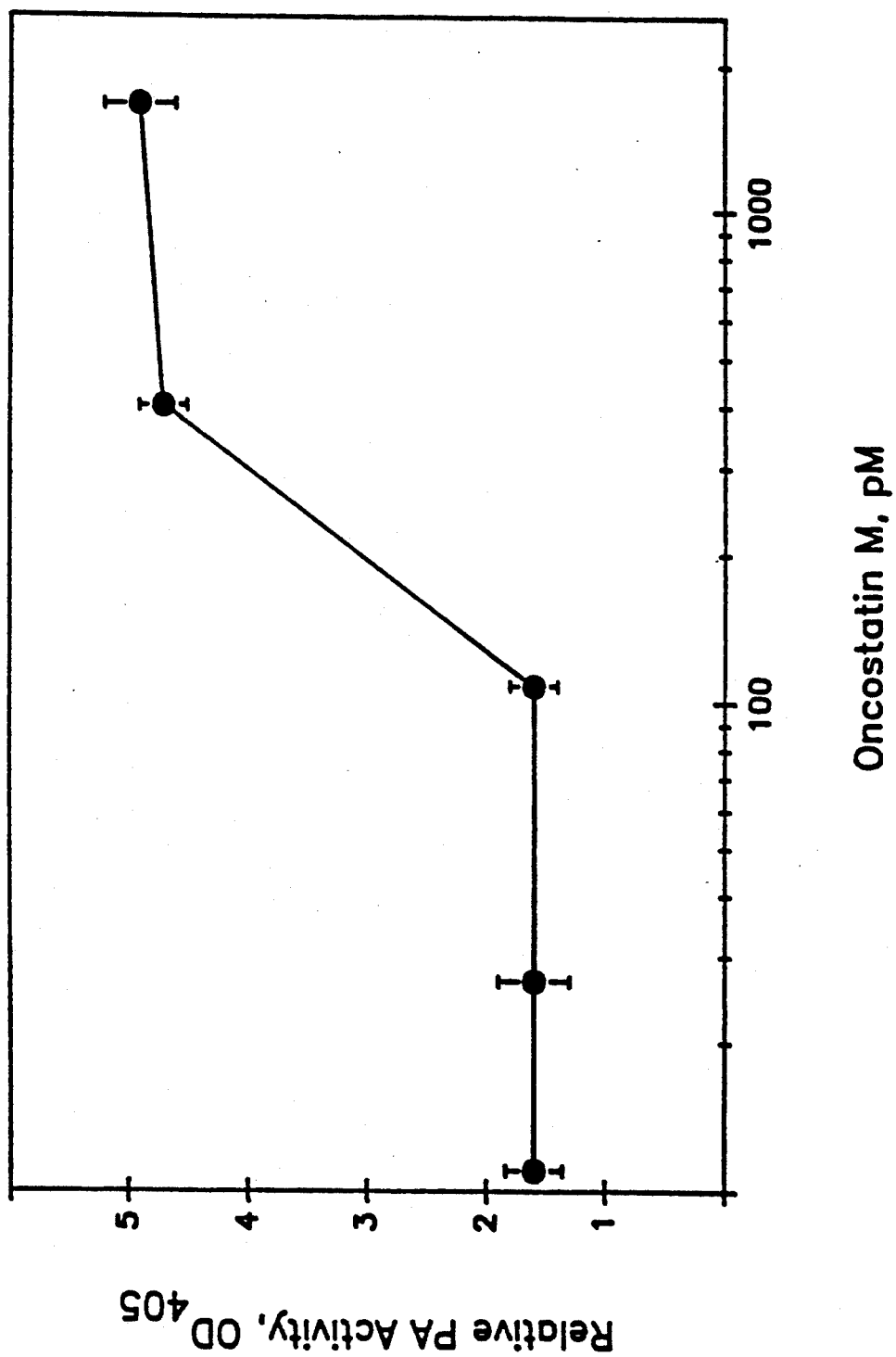
Figure 4B:
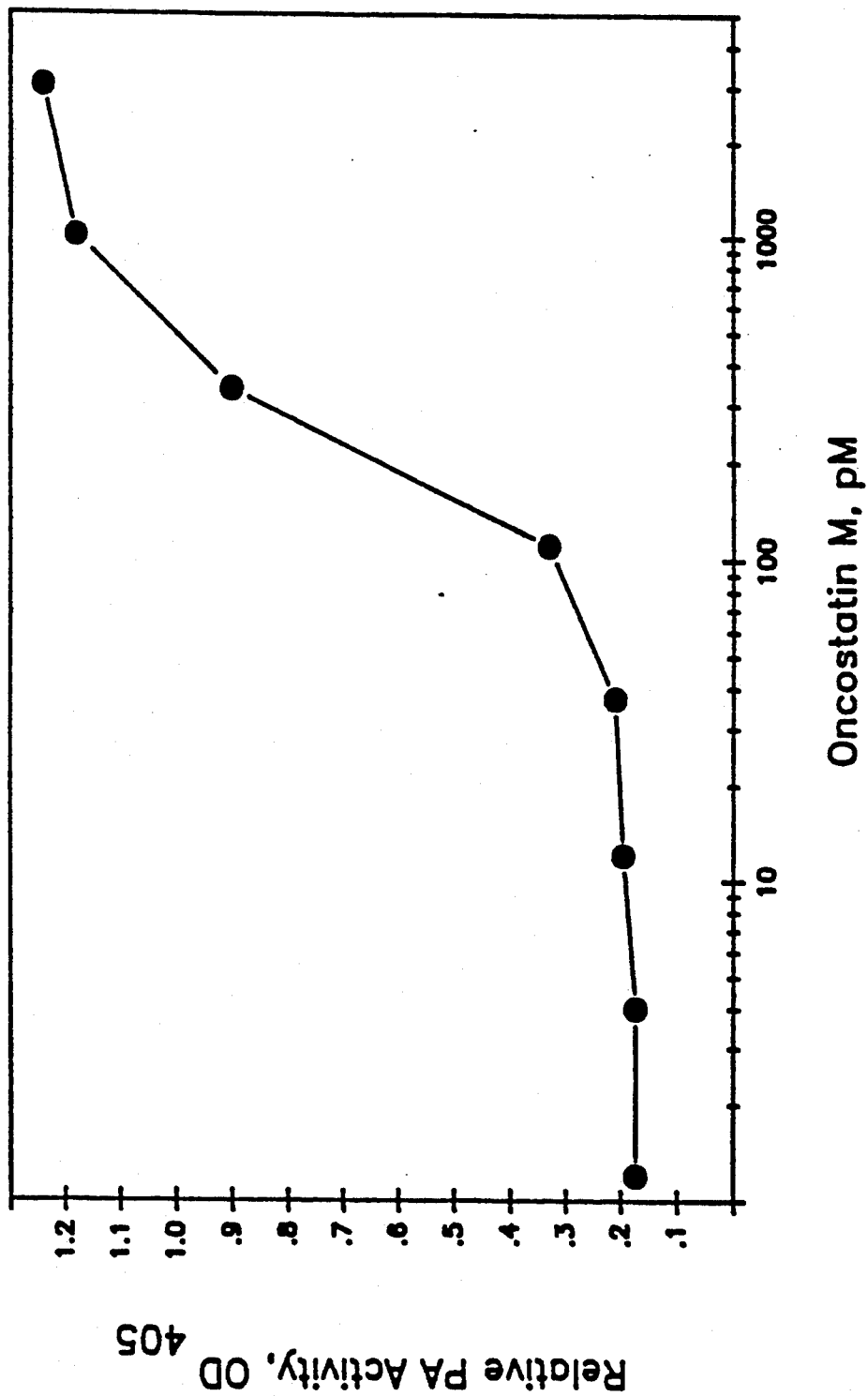

FIGS. 4A and 4B. Effective dose range for Oncostatin M stimulation of endothelial cell PA activity. BAECs were treated with varying concentrations of (FIG. 4A) native Oncostatin M (Zarlin et al.,1986, Proc. Natl. Acad. Sci. USA 38: 9739-9743) and (FIG. 4B) recombinant Oncostatin M. Cell-associated activity was determined as described in Section 7.1.2., infra.

Figure 5:
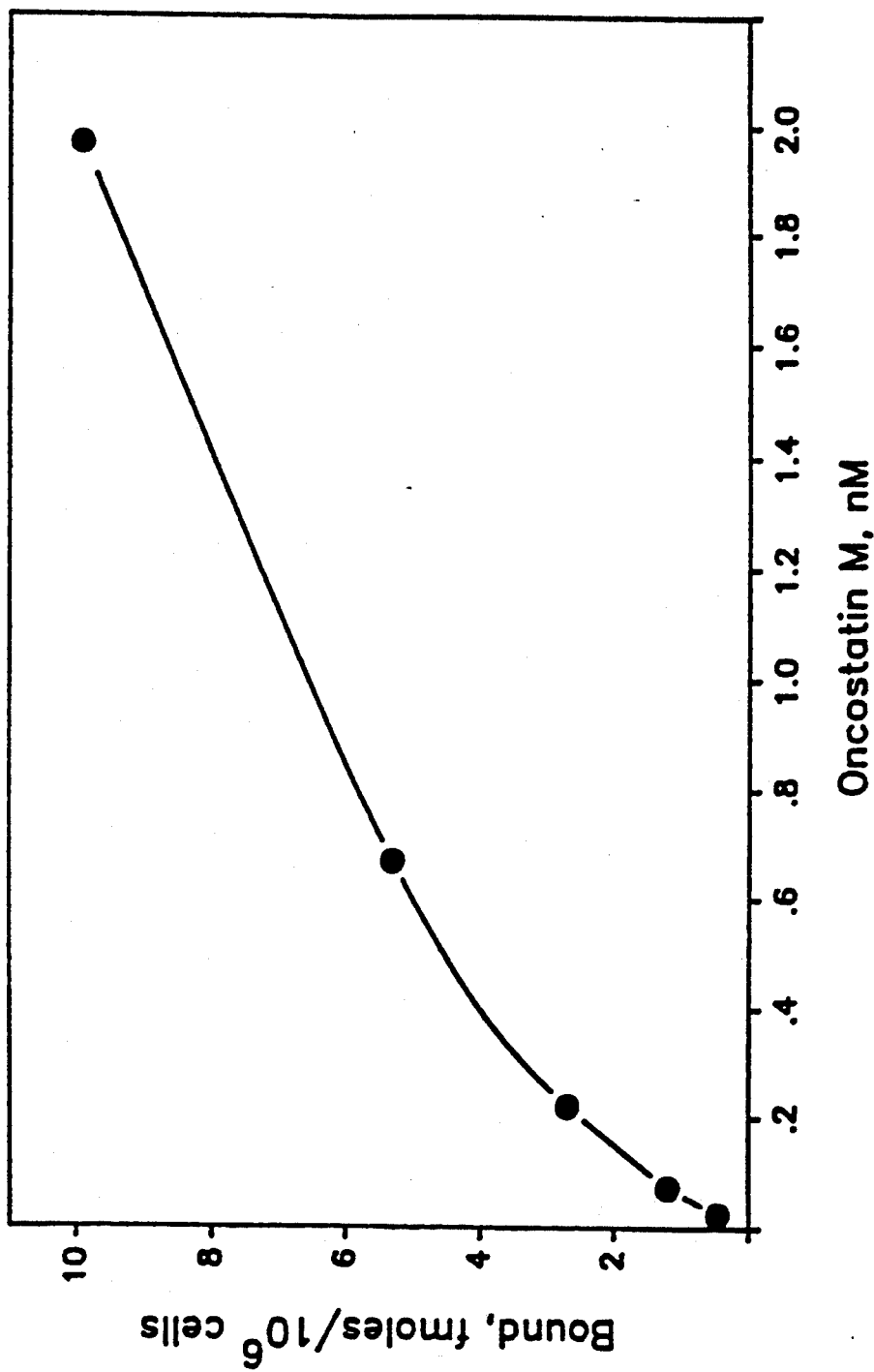

FIG. 5. Oncostatin M receptor binding saturation curve. The amount of Oncostatin M bound to BAECs is plotted against the amount applied demonstrating the saturable nature of Oncostatin M receptors on BAECs. Binding conditions were as described in Section 7.1.3., infra.

Figure 6:
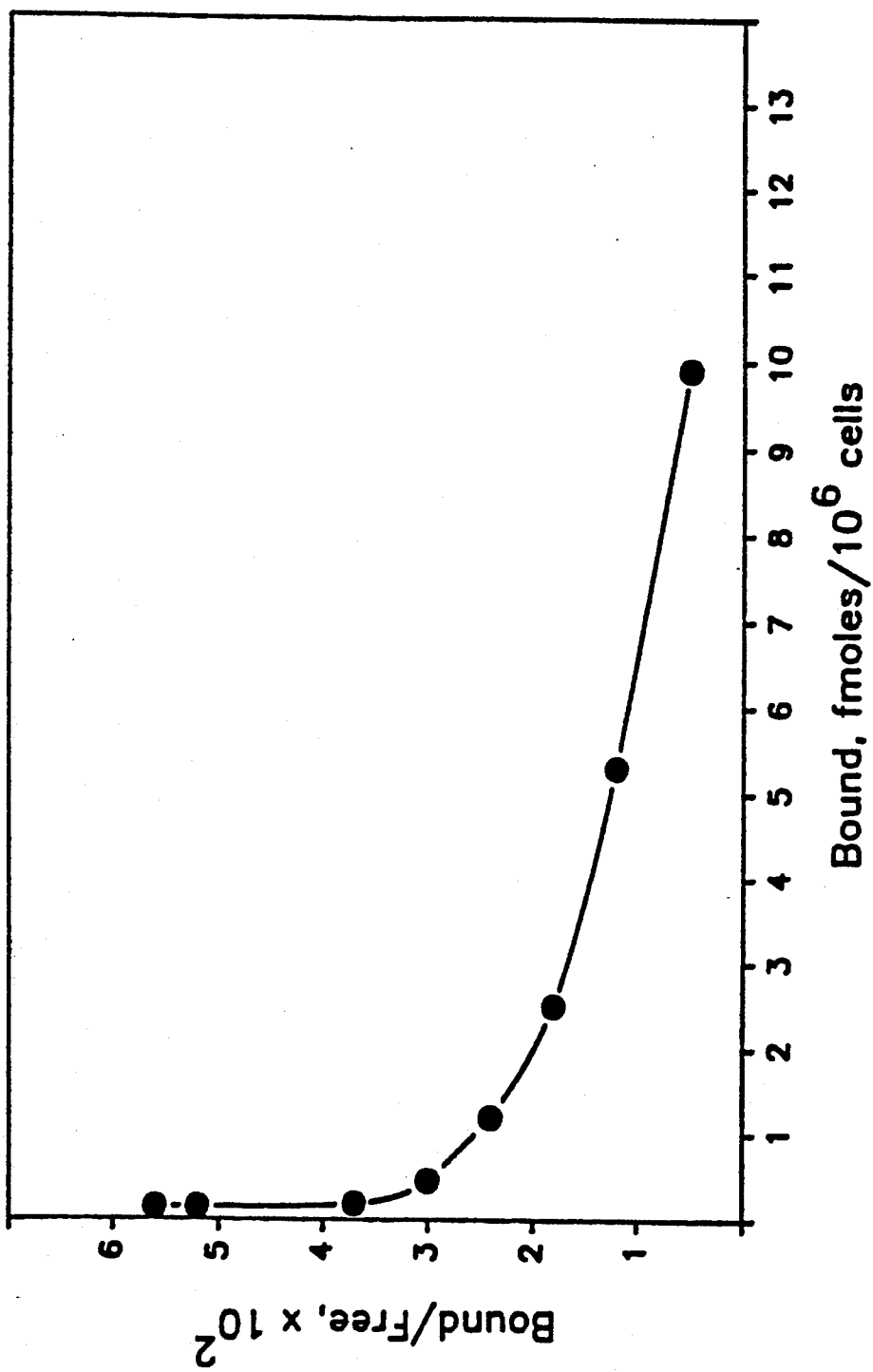

FIG. 6. Scatchard plot of BAEC Oncostatin M receptor binding data. Binding conditions were as described in Section 7.1.3., infra. Plot was analyzed as described in Section 7.2.2., infra.

Figure 7:
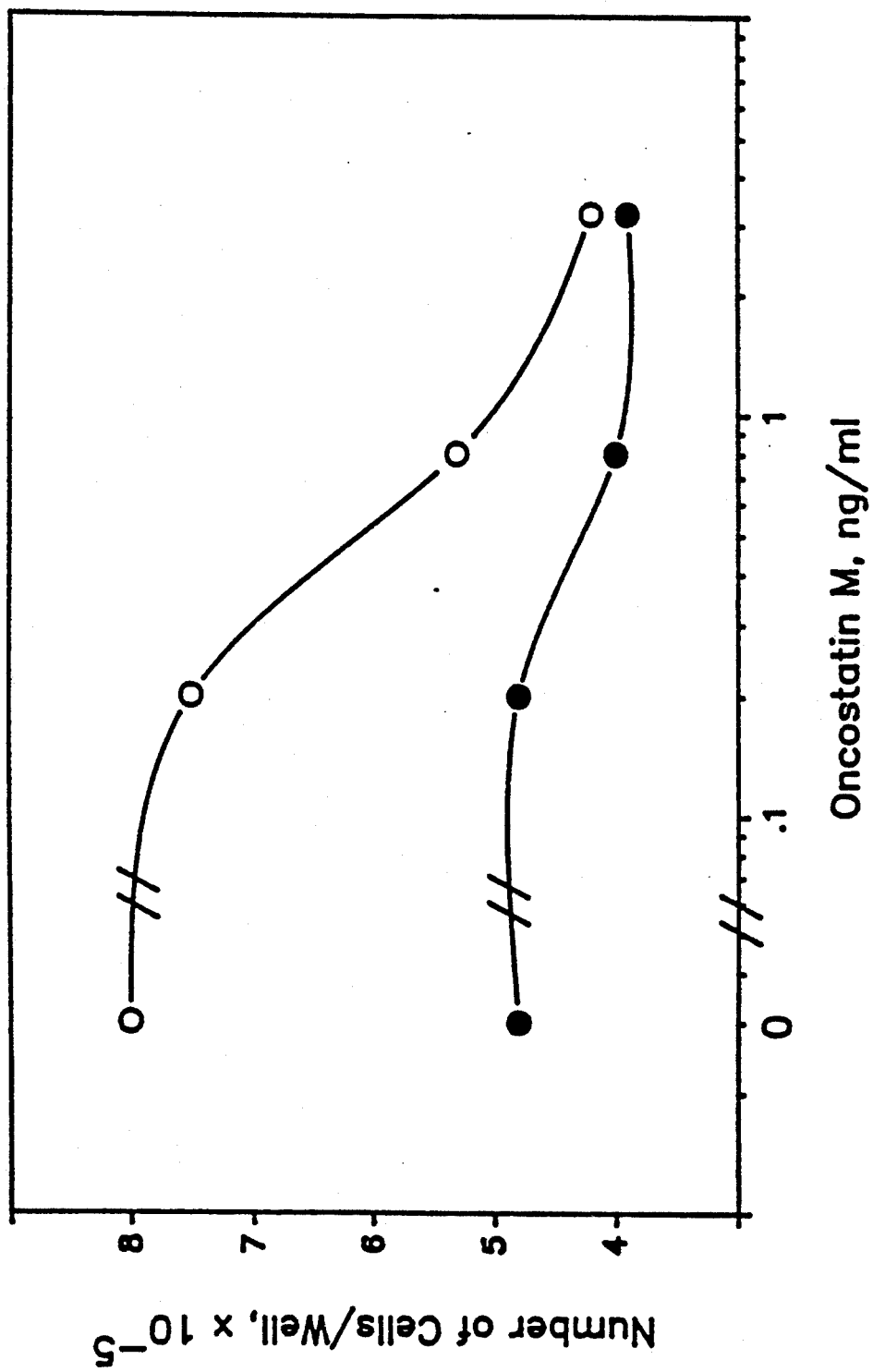

FIG. 7. Inhibition of endothelial cell growth by Oncostatin M. BAECs were grown to confluence in 24-well tissue culture plates with minimal essential media, MEM/F-10 (1:1), supplemented with 10% FBS (Hyclone). Serum-containing media was removed and monolayers washed twice with Dulbecco's PBS and replaced with fresh serum-free MEM/F-10. Triplicate wells were treated with varying doses of Oncostatin M alone (·) or in combination with 5 ng/ml bFGF (o). Following 3-day incubation at 37 degrees C., cell number was determined by hemacytometer counts. The difference in cell number at zero concentration Oncostatin M indicates the mitogenic response of these cells to bFGF.

Figure 8:
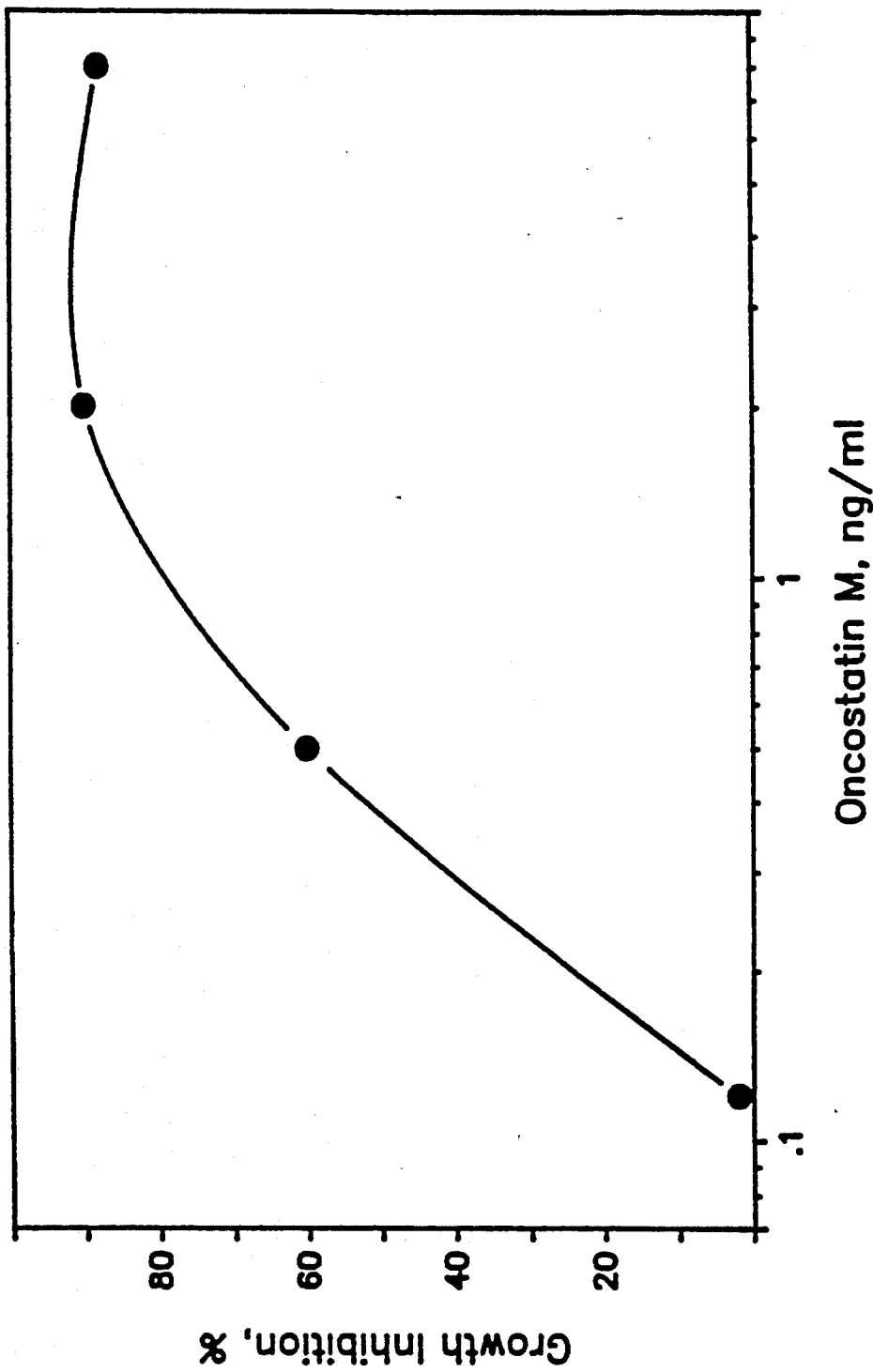

FIG. 8. Inhibition of bovine aortic endothelial cell growth by Oncostatin M. The growth inhibitory effect of Oncostatin M was quantified as described in Section 8.1., infra. The decrease in cell number resulting from Oncostatin M treatment is plotted as percent growth inhibition (number of untreated cells/well—number of treated cells/well divided by the number of untreated cells/well×100).

Figure 9:
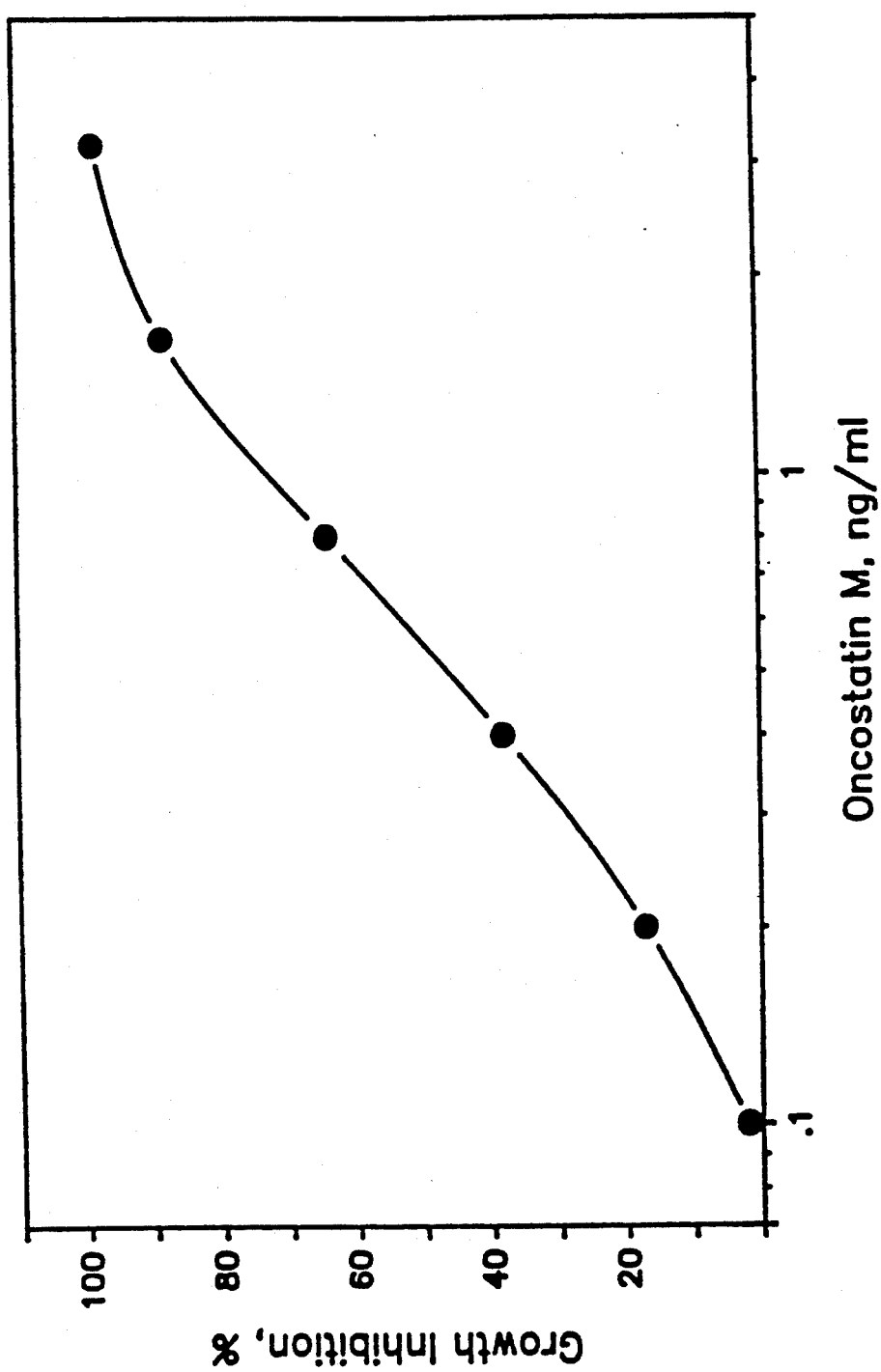

FIG. 9. Inhibition of bFGF-induced growth of fetal bovine heart endothelial cells as determined by the inhibition of DNA synthesis assay described in Section 8.1., infra. The decrease in incorporated radioactivity due to Oncostatin M treatment is plotted as percent growth inhibition (CPMs of untreated cells—CPMs of treated cells divided by CPMs of untreated cells×100).

FIGS. 10A and 10B. Photomicrographs of untreated BAECs (FIG. 10A) and BAECs treated with Oncostatin M (FIG. 10B) demonstrating the morphological effects of Oncostatin M on BAECs. Cell monolayers were examined for morphological alterations after 48 hours exposure to 400 pM Oncostatin M. Photomicrographs were taken at 250×magnification.

Figure 11:
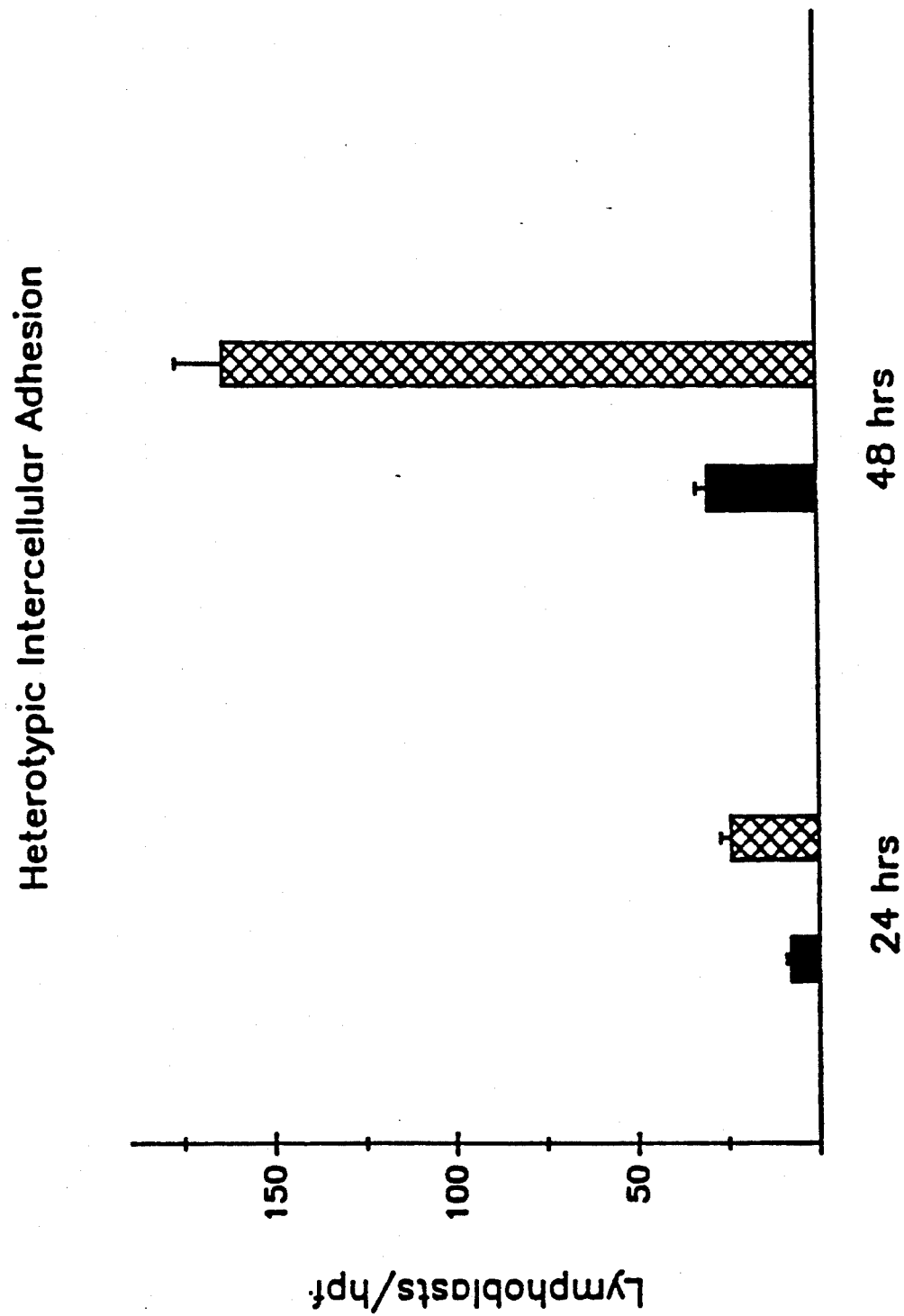

FIG. 11. Stimulation of leukocyte adhesion to bovine aortic endothelial cells by Oncostatin M treatment. Cells were treated as described in Section 9.2., infra. Lymphoblast binding was quantitated by averaging the number of cells observed in five randomly selected high power fields. The filled bars represent adhesion of lymphoblasts to untreated cells; crosshatched bars represent adhesion to Oncostatin M treated cells.

5. DETAILED DESCRIPTION OF THE INVENTION

The present invention is directed to methods for controlling endothelial cell proliferation and effector functions and to methods for the treatment of human vascular, immune and cell-growth disorders using Oncostatin M. The invention is based in part on the discovery that Oncostatin M mediates various biological effects on endothelial cells. The invention is described by way of examples in which the various biological effects of Oncostatin M on mammalian cells are determined using in vitro assay systems. The clinical implications of the biological effects mediated by Oncostatin M revealed and described herein may encompass a wide range of therapeutic uses of Oncostatin M pertaining to human vascular medicine, immunology, and cancer, and any such uses not specifically described or suggested herein are within the scope of the invention.

Oncostatin M, originally identified for its inhibitory effects on human tumor cell lines, was first isolated from phorbol 12-myristate 13-acetate (PMA)-induced human histiocytic lymphoma cells (Zarling et al., 1986, Proc. Natl. Acad. Sci. USA 83: 9739-9743) and from activated T lymphocytes (Brown et al., 1987, J. Immunol. 139: 2977-2983). The molecule is a heat and acid stable protein comprised of a single polypeptide chain of $M_r=28,000$. Like other naturally occurring growth regulators, Oncostatin M exhibits a variety of biological activities. Growth inhibition is observed with some, but not all, human tumor cell lines. In contrast, the growth of some normal fibroblasts, such as human foreskin fibroblasts or WI-38 cells, is stimulated by exposure to Oncostatin M (Zarling et al., 1986, Proc. Natl. Acad. Sci. USA 83: 9739-9743). The gene for Oncostatin M has been cloned and sequenced, and an active form of recombinant Oncostatin M has recently been expressed in mammalian cells (Copending application Ser. No. 144,574 filed Jan. 15, 1988, which is incorporated herein by reference in its entirety). The mature form, after cleavage of the signal peptide, is a glycoprotein containing 228 amino acids, five of which are cysteine residues. The protein has an extremely hydrophilic carboxy terminal domain. Although Oncostatin M is not structurally related to other known cytokines, its mRNA contains an AU-rich region at its 3′ untranslated end. This region in the Oncostatin M message is homologous to that of many cytokines, lymphokines and other growth-regulatory molecules, suggesting a common mode of regulating gene expression. A cellular receptor for Oncostatin M has been found on a variety of mammalian cells. The major Oncostatin M receptor molecule is a specific protein of Mr=150,000–160,000 (Lindsley et al, 1989, J. Biol. Chem. 264: 6528–6532).

In accordance with the invention, Oncostatin M may be obtained by techniques well known in the art from a variety of cell sources which synthesize bioactive Oncostatin M including, for example, cells which naturally produce Oncostatin M and cells transfected with recombinant DNA molecules capable of directing the synthesis and/or secretion of Oncostatin M. Alternatively, Oncostatin M may be synthesized by chemical synthetic methods including but not limited to solid phase peptide synthesis. Methods for the production of Oncostatin M are described in copending application Ser. No. 144,574 filed Jan. 15, 1988, a continuation-in-part of application Ser. No. 046, 846 filed May 4, 1987, a continuation-in-part of application Ser. No. 935,283 filed Nov. 26, 1986, a continuation-in-part of application Ser. No. 811,235 filed Dec. 20, 1985, each of which is incorporated by reference herein in its entirety.

In the practice of the method of the invention, the use of Oncostatin M obtained by any method, as well as the use of modified or truncated Oncostatin molecules and Oncostatin M analogs which retain the desired activity, are within the scope of the invention. In this regard, variations in the Oncostatin M primary structure, as well as variations in higher levels of structural organization, the type of covalent bonds linking the amino acid residues, and/or addition of groups to the terminal residues of Oncostatin M are within the scope of the invention. For example, the Oncostatin M molecule used in accordance with the invention may include conservative or non-conservative alterations in the amino acid sequence which result in silent changes that preserve the functionality of the molecule including, for example, deletions, additions and substitutions. Such altered Oncostatin M molecules may be desirable where they provide certain advantages in their use. As used herein, conservative substitutions would involve the substitution of one or more amino acids within the sequence of Oncostatin M with another amino acid having similar polarity and hydrophobicity/hydrophilicity characteristics resulting in a functionally equivalent molecule. Such conservative substitutions include but are not limited to substitutions within the following groups of amino acids: glycine, alanine; valine, isoleucine, leucine; aspartic acid, glutamic acid; asparagine, glutamine; serine, threonine; lysine, arginine; phenylalanine, tyrosine; and methionine, norleucine.

In another embodiment of the invention, Oncostatin M may be linked to carrier molecules. For example, Oncostatin M could be covalently coupled to an antibody molecule specific for endothelial cells or for some other cell surface antigen which will allow Oncostatin M to be targeted to cells which express that particular antigen. Similarly, Oncostatin M may be linked to other "targeting" molecules such as hormones, growth factors, cytokines, etc. In this way, the Oncostatin M molecule could be altered so that it is taken up by cells that may not express a receptor for the particular Oncostatin M molecule chosen for use. Such coupling techniques are well known in the art and can include, for example, the use of cross-linking agents, schiff-base formation, amide bonds, peptide bonds, sulfide bonds, etc.

To facilitate description, the present invention may be broadly classified with respect to its major aspects; specifically, the use of Oncostatin M to (1) modulate immunity, (2) enhance plasminogen activator and fibrinolytic activity, and (3) control angiogenesis. These divisions are made solely for the purpose of description and are in no way intended to limit or restrict the scope of the specification or the appended claims.

5.1. Oncostatin M As an Immunomodulator

One aspect of the present invention relates to the use of Oncostatin M as an immunomodulator in the treatment of human autoimmune and alloimmune diseases. In this regard, applicants have discovered through a series of experiments such as those described in Section 6., et seg. that Oncostatin M is capable of inhibiting the expression of class I and II HLA antigens on the surface of human endothelial cells in vitro. Therefore, Oncostatin M may find use in decreasing the immunogenicity of endothelial tissue to helper and/or effector T lymphocytes.

5.1.1. Use of Oncostatin M in Organ Tranplantation

Since class I molecules appear to be the initial target for cytotoxic T lymphocytes, depression in class I expression would be expected to prevent or inhibit the onset of strong secondary responses. Perhaps more importantly, the inhibition of class II expression on endothelial cells may block the recruitment of antigen-specific, gamma-interferon-secreting helper T lymphocytes, thus thwarting the development of immune response. In a particular embodiment of the invention, compounds containing effective doses of Oncostatin M formulated in suitable pharmacological carriers may be administered to organ transplant recipients such as kidney, heart and lung transplant recipients, via any appropriate route including but not limited to local or systemic injection, in order to inhibit or prevent the expression of HLA antigens and rejection of the transplant. In addition, Oncostatin M may be linked to a carrier or targeting molecule and/or incorporated into liposomes, microcapsules, and controlled release preparations prior to administration in vivo. Through a series of experiments, such as those described in Section 6, infra, applicants have determined that endothelial cell expression of class I and II MHC antigens, particularly gamma-interferon- and tumor necrosis factor-alpha-stimulated expression, is specifically antagonized by Oncostatin M at concentrations ranging from 1–50 ng/ml. For example, at a concentration of 5 ng/ml, Oncostatin M inhibited IFN-$\gamma$-stimulated class I antigen expression by 51% and TNF-$\alpha$-stimulated expression by a striking 141%. Induction of class II antigen expression by IFN-$\gamma$ was inhibited by as much as 84%. When used in combination with a synergistic cytokine such as TGF-$\beta$, low concentrations of Oncostatin M were effective in producing strong inhibitory effects. In addition, applicants' research data suggests that Oncostatin M is incapable of inhibiting class I or class II HLA antigen expression on cells of the monocyte/macrophage lineage. Use of Oncostatin M may therefore offer a better alternative to Cyclosporin A. The broad effects of Cyclosporin A, currently the principal immunosuppressive agent used in allograft transplantations, results from the inhibition of T lymphocyte proliferation generally. Oncostatin M does not have a similar effect on T cell proliferation.

In accordance with this aspect of the invention, Oncostatin M may be used alone or in combination with one or more other cytokines, growth factors or immunosuppressive agents including but not limited to TGF-β, Cyclosporin A and corticosteroids in order to increase the likelihood of a transplant recipient's acceptance of the donor organ. Applicants have in this regard observed that TGF-β acts synergistically with Oncostatin M to strongly inhibit the expression of HLA antigens on IFN-γ-stimulated endothelial cells. As little as 50 pg/ml Oncostatin M in combination with 0.5 ng/ml TGF-β resulted in a nearly 50% reduction of class I antigen expression (Section 6.2.2., infra). Furthermore, the expression of IFN-γ-stimulated class II antigens was inhibited 80% by the combination of 0.5 ng/ml Oncostatin M and 1 ng/ml TGF-β.

5.2. Use of Oncostatin M to Induce A Fibrinolytic Phenotype in Vascular Endothelium Another aspect of the invention is directed to the use of Oncostatin M to shift and/or maintain the balance between the constitutive antithrombogenic and the inducible procoagulant phenotypes of endothelium in favor of the antithrombogenic phenotype. The results described in Section 7, infra indicate that Oncostatin M dramatically and specifically stimulates the expression of PA activity in endothelial cells in vitro, resulting in elevated levels of bioactive plasmin. These findings suggest that Oncostatin M may be useful in inducing increased endothelial cell-mediated fibrinolysis.

It is known that endothelial cells generally inhibit thrombus formation, and that this effect is mediated by four different pathways, one of which is fibrinolysis. Endothelial cells are actively involved in fibrinolysis through the release of plasminogen activators. Oncostatin M may therefore be useful in the treatment of thrombotic cardiovascular diseases. For example, patients treated for acute myocardial infarction (AMI) with urokinase, streptokinase, or t-PA may benefit from concurrent and/or sustained treatment with Oncostatin M in order to reduce the likelihood of recurrent thrombi. Also, the ability of Oncostatin M to shift the endothelial surface to a more fibrinolytic phenotype may be useful in the treatment of a variety of other Disseminated Intravascular Coagulation (DIC) syndromes such as deep vein thrombosis, pulmonary embolism, peripheral arterial thromboembolism, hemolytic uremic syndrome and thrombotic thrombocytopenic purpura. Effective doses of Oncostatin M formulated in suitable pharmacological carriers may be administered in vivo via any appropriate route including but not limited to injection, infusion and selective catheterization. In addition, Oncostatin M may be linked to a carrier or targeting molecule and/or incorporated into liposomes, microcapsules, and controlled release preparations prior to administration in vivo.

The ability of Oncostatin compositions to stimulate PA, leading to fibrinolysis or other important foci of PA activity, can readily be tested using in vitro assay systems such as the PA activity assay described in Section 7 et seg. herein. The functional equivalence and/or increased efficacy of modified Oncostatin M molecules or Oncostatin M analogs may be evaluated similarly. In addition to testing the effects of Oncostatin M compounds on endothelial cells, other cell types may be assayed for their responsiveness to the PA activity-inducing property of Oncostatin M.

5.3. Use of Oncostatin M to Control Angiogenesis

Yet another aspect of the invention is directed to the use of Oncostatin M to inhibit neovascularization in pathological angiogenic conditions including but not limited to cancer. Applicants believe that Oncostatin M compounds may strongly inhibit neovascularization in such conditions based on results from in vitro studies, such as those described in Section 8., infra, demonstrating that Oncostatin M blocks the response of endothelial cells to proliferative stimuli (i.e., bFGF). Moreover, unlike other cytokines which inhibit angiogenesis, Oncostatin M is not chemotactic for monocyte-macrophages (Section 9., infra) and therefore is not likely to initiate angiogenesis in vivo via secondary effects on leukocyte recruitment.

Oncostatin M may be useful in the treatment of Kaposi's sarcoma (KS). KS appears to be derived from endothelial cells (Jones et al., 1986, J. Clin. Pathol. 39: 742; Macher, 1988, Public Health Report 103: 246) and may therefore be susceptible to the anti-proliferative effects of Oncostatin M. Similarly, Oncostatin M may also be useful in the treatment of many other diseases associated with angiogenesis including, for example, diabetic retinopathy, glaucoma, hemangioma and various cancers. In a specific embodiment of the invention, compounds containing effective doses of Oncostatin M formulated in suitable pharmacological carriers may be administered to patients suffering from diseases associated with angibgenesis via any appropriate route including but not limited to injection, topical application, etc., in order to inhibit neovascularization and the progression of the disease. In addition, Oncostatin M may be linked to a carrier or targeting molecule and/or incorporated into liposomes, microcapsules, and controlled release preparations prior to administration in vivo. The ability of Oncostatin M compositions to inhibit neovascularization may be assessed using in vitro assay systems such as the growth inhibitory and chemotactic assays described in Section 8 et seg. herein. The functional equivalence and/or increased efficacy of modified Oncostatin M molecules or Oncostatin M analogs may be evaluated similarly.

6. EXAMPLE: MODULATION OF ENDOTHELIAL CELL HLA ANTIGEN EXPRESSION BY ONCOSTATIN M IN VITRO

The in vitro experiments described below demonstrate, inter alia, that Oncostatin M inhibits the cytokine-stimulated expression of class I and class II HLA antigens on human endothelial cells, but not on monocyte-macrophages, and that TGF-β synergizes with Oncostatin M to produce this inhibitory effect.

6.1. Materials and Methods

6.1.1. Endothelial Cell Cultures

Human umbilical vein endothelial cells (HUVEC) were isolated from umbilical vein as described (Wall et al., 978, J. Cell. Physiol. 96: 203). Cells were passaged with collagenase and grown to confluence on gelatin-coated plasticware in CS-1 defined serum free medium (Cell Systems, Kirkland, Wash.) substituted with 50 μg/ml heparin and recombinant ECGS (Bionetics). Cells were given fresh unsupplemented media at least 12 hours prior to experimentation.

6.1.2. Immunostaining

Several fluorescein-labeled monoclonal antibodies (MAbs) were employed for the detection of class I and class II HLA antigens: HIDE (Gladstone et al., *Histocompatability Testing*, 429, Dupont, Ed., 1984) was used for the detection of class I HLA antigens; a DR-specific antibody, VI.15 ( Gladstone et al., 1982, Proc. Natl. Acad. Sci. USA 79: 1235), was used for the detection of class II HLA-DR antigen; antibody 33.1 was used for the detection of HLA-DQ antigens and was provided by G. Marti (Marti et al., 1983, J. Exp. Med. 158: 1924–1983); HB10a was used for the detection of class II HLA-DR and HLA-DP antigens and was provided by Dr. E. Clark (Regional Primate Research Center at Washington University, Seattle, Wash.).

6.1.3. Quantitative Antigen Assay

The expression of cell surface HLA antigens was measured essentially as described (Gladstone et al., 1982, Proc. Natl. Acad. Sci. USA 79: 1235–39) with modifications for fluorescent activated cell sorter (FACS) analysis (Basham and Merigan, 1983, J. Immunol. 130: 1492). Briefly, $5 \times 10^4$ cells per sample were immunostained and HLA antigen expression quantified by indirect immunofluorescence using a FACS analyzer. MAbs were incubated for 45 minutes in each step. Sample populations were compared by mean channel fluorescence on a four decade logarithmic scale and, where appropriate, linear fluorescence equivalents were obtained by conversion.

6.1.4. Cytokines

Recombinant Oncostatin M was prepared as described (Malik et al., 1989, Mol. Cell. Biol., in press), recombinant TGF-β as described in Gentry et al., 1987, Mol. Cell. Biol. 7: 3418), recombinant IFN-γ and TNF-α were purchased from Amgen Inc. Natural Oncostatin M was prepared as described in (Zarling et al., 1986, Proc. Natl. Acad. Sci. USA 38: 9737).

6.1.5. Oncostatin M Receptor Assay

Highly purified human recombinant Oncostatin M was radiolabeled by the IODO-GEN procedure (Fraker and Speck, 1978, Biochem. Biophys. Res. Comm. 80: 849) to a specific activity of 52 μCi/μg. Radioreceptor assays were conducted in situ on confluent monolayers of HUVECs grown in 24-well tissue culture plates ($10^5$ cells/well) in duplicate. Monolayers were first washed twice with binding buffer (Dulbecco's MEM+0.1% bovine serum albumin+15 mM HEPES) and then 250 μl binding buffer containing 1 ng/ml radiolabeled Oncostatin M and variable amounts of unlabeled Oncostatin M were added to the monolayers. Cells were incubated at 23 degrees C. for 3 hours to maintain steady state binding (Lindsley et al., 1988, J. Biol. Chem. 264: 4282). Following the incubation period, cells were washed with cold binding buffer and solubilized in 1N NaOH. Radioactivity was detected by a gamma spectrophotometer and data plotted according to the method of Scatchard (Scatchard, 1949, Ann. N.Y. Acad. Sci. 51: 660). Non-specific binding was measured in the presence of a 400-fold molar excess of unlabeled Oncostatin M.

6.2. Results

6.2.1. Oncostatin M Inhibits Cytokine-Stimulated HLA Antigen Expression on Human Endothelial Cells The capacity of Oncostatin M to modulate the regulation of HUVEC MHC antigen expression by other cytokines was evaluated by indirect immunofluorescence and FACS quantitation as described in Materials and Methods, supre. Table I presents the effects of various cytokines on HUVEC HLA antigen expression. At a concentration of 100 U/ml, both IFN-γ and TNF-α significantly affected the expression of class I antigen, amplifying expression by fivefold and twofold respectively. Additionally, IFN-γ amplified class II antigen expression by greater than sixfold. In contrast, neither TGF-β nor Oncostatin M were able to amplify class I or class II expression.

TABLE I[1]

| CYTOKINE | H9 (control IgG) | CLASS I (HLA-A,B,C) | CLASS II (HLA-DR,DP) |
|---|---|---|---|
| None | 2.3 | 39 | 2.9 |
| IFN-γ, 100 U/ml | 2.4 | 200 | 18.6 |
| TNF-α, 100 U/ml | 2.6 | 91 | 3.7 |
| TGF-β, 50 ng/ml | 2.4 | 37 | 2.7 |
| Onco M, 50 ng/ml | 2.4 | 29 | 3.1 |

EFFECTS OF VARIOUS CYTOKINES ON HUVEC HLA ANTIGEN EXPRESSION

[1]Values expressed in linear fluorescence equivalents

Table II presents the effects of different concentrations of Oncostatin M on the cytokine-induced expression of class I and class II antigens. Oncostatin M antagonized IFN-γ- and TNF-α-stimulated HLA antigen expression in a dose dependent manner. At a concentration of 5 ng/ml, Oncostatin M inhibited IFn-γ-stimulated class I HLA-A,B,C anitgen expression by 51% and TNF-α-stimulated expression by 141%. Induction of class II HLA-DR and HLA-DQ antigens by IFN-γ was inhibited 84% and 72%, respectively, with 50 ng/ml Oncostatin M. These results strongly indicate that Oncostatin M may be useful in down-modulating the immunogenicity of endothelial cells in vivo.

TABLE II[1]

EFFECTS OF ONCOSTATIN M ON CYTOKINE-INDUCED HLA ANTIGEN EXPRESSION

| CYTOKINE | CLASS I (HLA-A,B,C) | CLASS II (HLA-DR) | CLASS II (HLA-DQ) |
|---|---|---|---|
| None | 30 | 2 | 3 |
| IFN-γ, 100 U/ml | 113 | 21 | 3 |
| +Onco M, 0.05 ng/ml | 119 | 19 | — |
| +Onco M, 0.5 ng/ml | 80 | 11 | — |
| +Onco M, 5.0 ng/ml | 17 | 7 | — |
| +Onco M, 50.0 ng/ml | — | 5 | 8 |
| None | 71 | | |
| TNF-α, 100 U/ml | 125 | | |
| +Onco M, 0.05 ng/ml | 125 | | |
| +Onco M, 0.5 ng/ml | 76 | | |
| +Onco M 5.0 ng/ml | 49 | | |

[1]Values expressed in linear fluorescent equivalents

6.2.2. Synergistic Action of Oncostatin M and TGF-β

The effects of Oncostatin M, TGF-β, and Oncostatin M/TGF-β on IFN-γ-treated endothelial cells were evaluated and compared in order to determine whether synergistic action between TGF-β and Oncostatin M exists. The results of these experiments are illustrated in FIGS. 1A and 1B. TGF-β alone demonstrates a weak capacity for inhibiting IFN-γ-stimulated expression of either class I HLA-A,B,C or class II HLA-DR antigens. However, suboptimal amounts of Oncostatin M in combination with TGF-β resulted in synergistic antagonism of class I and class II antigen expression. For example, 50 pg/ml Oncostatin M and 0.5 ng/ml TGF-β in combination resulted in a 49% inhibition of class I antigen expression whereas independent treatment with the same concentration of Oncostatin M or TGF-β resulted in 7% and 15% inhibition respectively (FIG.

1A). Similarly, the combination of 0.5 ng/ml Oncostatin M and 1 ng/ml TGF-$\beta$ resulted in an 80% inhibition of class II HLA-DR expression whereas independent treatments at these concentrations resulted in 13%(Oncostatin M) and 26%(TGF-$\beta$) inhibitions (FIG. 1B). Therefore, with respect to the inhibition of both class I and class II antigen expression, a synergistic effect some two times greater than the predicted additive effect was observed, suggesting compositions containing both TGF-$\beta$ and Oncostatin M may be particularly useful.

6.2.3. Tissue Specificity of Oncostatin M Effect on HLA Expression

In order to explore whether the inhibitory effect of Oncostatin M on HLA antigen expression is specific for endothelial cells, the capacity of Oncostatin M to antagonize the expression of cytokine-induced class II MHC antigen expression on monocytes and macrophage-like cells was determined.

Human monocytes were isolated from blood using Ficoll gradients and adhered to plastic culture dishes. Cells were assayed for class II antigen as described in Materials and Methods. Cells were treated with 100 and 250 U/ml IFN-$\gamma$ to boost basal levels of class II HLA antigens and parallel cultures were also treated with 5 ng/ml Oncostatin M. After a 3 day incubation, cells were stained with fluorescein-labeled antibodies and analyzed by indirect immunofluorescence and FACS quantitation as described in Materials and Methods, supra. The results indicate that Oncostatin M has no effect on either the basal or cytokine-induced levels of class II HLA antigen expression.

In another experiment, the effects of 1-10 ng/ml recombinant Oncostatin M on class II MHC antigen expression in a murine macrophage-like cell line (Wehi-3 cells) were investigated similarly. Class II antigen expression is strongly induced by either IFN-$\gamma$ or TNF-$\alpha$ in these cells (Chang and Lee, 1968, J. Immunol. 137: 2853). As, in the case of human monocytes, Oncostatin M had no effect on the basal or cytokine-induced levels of class II HLA antigen expression in these cells.

Since these results suggest that Oncostatin M is incapable of inhibiting class II HLA antigen expression on cells of the monocyte/macrophage lineage, Oncostatin M may offer a therapeutically more specific alternative to the broad immunosuppressive effects induced by other compounds such as Cyclosporin A, corticosteroids, and cyclophosphamides.

6.2.4. High Level Epression of Oncostatin M Receptors on HUVECs

HUVECs were grown to confluence in 24-well tissue culture dishes and radioreceptor assays conducted as described in Section 6.1.5., supra. FIG. 2A presents the saturation curve and FIG. 2B presents the Scatchard plot for Oncostatin M binding to HUVECs. Binding is saturable and the Scatchard plot shows a curvilinear isotherm indicating the presence of at least two classes of cell-surface binding sites on HUVECs (similar results were obtained with bovine endothelial cells, Section 7.2.2., infra). When analyzed by the two site model, a total concentration of 380,000 Oncostatin M receptor binding sites per cell were calculated, comprising 1,700 high affinity sites (Kd=5.6 pM) and 378,300 low affinity sites (Kd=8.5 nM). Half-maximal receptor occupancy occurred at 2 ng/ml (67 pM) which correlates with the ED$_{50}$ of Oncostatin M inhibition of cytokine-induced HLA antigen expression (Section 6.2.1., supra. These human endothelial cells appear to express approximately ten times more Oncostatin M receptors than bovine endothelial cells (Section 7.2.2., infra).

The Oncostatin M receptor on HUVECs was further characterized by chemically cross-linking [$^{125}$I]-Oncostatin M to its receptor and analyzing the structural properties of the complex by polyacrylamide gel electrophoresis as described (Lindsley et al., 1989, J. Biol. Chem. 264: 4282–4289). As shown in the autoradiograph in FIG 2B, cross-linked ligand-receptor complex migrated on a 6% SDS-PAGE under reducing conditions as a prominent 180,000 molecular weight band (lane 3). The inclusion of 400-fold molar excess of unlabeled Oncostatin M during the binding period specifically competed out the radioactivity associated with this band (lane 4). Therefore, applicants conclude that the Oncostatin M receptor on human endothelial cells is similar in structure and function to the Oncostatin M receptor on bovine endothelial cells, as well as to the Oncostatin M receptor on human cells of non-endothelial origin (lanes 1 and 2).

7. INDUCTION OF FIBRINOLYTIC ACTIVITY IN AORTIC ENDOTHELIAL CELLS BY ONCOSTATIN M

The experiments described below demonstrate that Oncostatin M induces endothelial cell-associated fibrinolysis in vitro.

7.1. Material and Methods

7.1.1. Cell Culture

Bovine aortic endothelial cells (BAEC) were prepared as described (Schwartz, 1978, In Vitro 4: 966–980) and cultured as follows. BAECs were grown at 37 degrees C. to confluence in 24-well tissue culture plates (4×10$^5$ cells) with minimal essential medium (MEM/F-10 1:1) supplemented with 10% fetal bovine serum. Serum-containing medium was removed, monolayers washed twice in Dulbecco's phosphate buffered saline (PBS) and replaced with fresh serum-free MEM/F-10 prior to treating the cells with cytokines and assaying for plasminogen activator activity. Determinations of plasminogen activator (PA) activity were made following 72 hour incubations with cytokines at 37 degrees C./ 95% CO$_2$-air atmosphere. Cell viability was greater than 98% as determined by trypan blue dye exclusion. Cells numbers were determined by hemacytometer counts.

7.1.2. Plasminogen Activator Activity Assay

Plasminogen activators (PA) catalyze the conversion of plasminogen to the active protease plasmin which acts directly to cleave fibrin molecules. The following assay employs plasminogen as the substrate for activation by PA, which activation is measured by detecting resulting fibrinolytic activity on a synthetic peptide.

Following treatment of BAECs with various cytokines, conditioned media was removed and stored at −70 degrees C. for subsequent analysis. Monolayers were washed twice with PBS and tested for cell-associated PA activity using a two-step enzyme assay (Searls, 1980, Analyt. Biochem. 107: 64). Briefly, duplicate wells were incubated for 1 hour at 37 degrees C. with saturating quantities of plasminogen substrate in 300 $\mu$l serum-free medium. An equal volume of a synthetic chromogenic peptide, H-D-val-leu-lys-p-NA (Kabi Virtum, Sweden), at 1 mg/ml in 210 mM lysine buffer, pH 8.9, was then added and cells were allowed to incubate further for up to 2 hours. The synthetic peptide comprises the sequence of the fibrin molecule recognized and cleaved by plasmin. Proteolytic cleavage by plasmin releases p-nitroanaline from the peptide which can be detected spectrophotometrically. Thus, the assay is designed to measure changes in plasminogen activator activity by measuring plasminogen-dependent lysis of the synthetic peptide.

Enzyme activity was quantified by measuring liberated p-nitroanaline on a spectrophotometer at 405 nm and calibrated by comparison with a standard of 0.025 Plough Units purified uPA (Calbiochem) run in parallel with the cell samples. Optical density (OD) values were normalized to cell number and expressed as relative PA activity per $10^6$ cells. To determine the level of secreted PA activity by BAECs, the conditioned media was thawed, clarified by centrifugation, and 200 μl aliquots analyzed as described above.

7.1.3. Oncostatin M Receptor Assay

Highly purified human Oncostatin M was radiolabeled by the IODO-GEN procedure (Fraker and Speck, 1978, BBRC 80:849) to a specific activity of 52 μCi/μg. Radioreceptor assays were conducted in situ on confluent monolayers of BAECs grown in 24-well tissue culture plates ($4 \times 10^5$ cells/well) in duplicate. Monolayers were first washed twice with binding buffer (Dulbecco's MEM+0.1% bovine serum albumin+15 mM HEPES) and then 250 μl binding buffer containing 1 ng/ml radiolabeled Oncostatin M and variable amounts of unlabeled Oncostatin M were added to the monolayers. Cells were incubated at 23 degrees C. for 3 hours to maintain steady state binding (Lindsley et al., 1989, J. Biol. Chem. 264: 4282). Following the incubation period, cells were washed with cold binding buffer and solubilized in IN NaOH. Radioactivity was detected by a gamma spectrophotometer and data plotted according to the method of Scatchard (Scatchard, 1949, Ann. N.Y. Acad. Sci. 51: 660). Non-specific binding was measured in the presence of a 400-fold molar excess of unlabeled Oncostatin M.

7.2. Results

7.2.1. Specific Stimulation of Plasminogen Activator Activity By Oncostatin M To determine the effect of Oncostatin M on the regulation of endothelial cell-mediated fibrinolytic activity, the ability of Oncostatin M to induce the synthesis of plasminogen activators (PAs) capable of catalyzing the conversion of plasminogen to bioactive plasmin was examined. Elevated PA levels, resulting in a corresponding increase in bioactive plasmin levels, was detected on Oncostatin treated BAECs as well as in treated cell supernatants.

The results presented in Table III indicate that Oncostatin M dramatically and specifically stimulates the expression of PA activity. Conditioned media collected from Oncostatin M treated cells exhibited more than 12 times more PA activity than conditioned media from untreated cells. In addition, Oncostatin M specifically induced plasminogen-dependent fibrinolytic activity rather than a protease capable of directly cleaving the synthetic peptide; conditioned media from Oncostatin M-treated cells with plasminogen substrate generated 76 times more activity than treated conditioned media alone. These results show that Oncostatin M specifically induces the synthesis and/or secretion of active plasminogen activator molecules and/or inhibits the expression or function of plasminogen activator inhibitors (PAI1 and PAI2).

TABLE III[1]

| STIMULATION OF PA ACTIVITY BY ONCOSTATIN M | |
|---|---|
| TEST SAMPLE | $OD_{405}$ |
| Fresh MEM/F-10 alone | 0.005 |
| Fresh MEM/F-10 + U-PA | 0.004 |
| Plasminogen alone | 0.000 |
| Plasminogen + u-PA | 0.180 |
| CM[2] from untreated BAECs alone | 0.002 |
| CM from untreated BAECs + plasminogen | 0.080 |
| CM from Oncostatin M-treated BAECs alone | 0.013 |
| CM from Oncostatin M-treated BAECs + plasminogen | 0.985 |

[1]BAECs ($3 \times 10^5$ cells) were treated for 27 hours with 900 pM Oncostatin M and the level of plasminogen-dependent proteolytic activity released into the media determined as described in Section 7.1.2.
[2]Conditioned media In order to ascertain which form of plasminogen activator activity may be stimulated by Oncostatin M treatment (t-PA or u-PA), BAECs were preincubated with a neutralizing anti-u-PA monoclonal antibody prior to measuring cell-associated activity. Cells were washed twice in fresh serum free media and incubated for 1 hour at 23 degrees C. in the presence or absence of 30 μg/ml anti-u-PA antibody (purified MAb 4BID8-3.1; Gladstone and Enghart, manuscript in preparation) in a total volume of 300 μl. Following incubation, the cells were again washed and PA activity assayed as described in Materials and Methods, supra. Cells treated with 2.7 nM Oncostatin M for 72 hours measured an $OD_{405}$ of 5.51 without antibody preincubation and 2.65 following antibody preincubation, a decrease of 52%. Therefore, Oncostatin M appears to cause a significant increase of u-PA expression and possibly an increase in t-PA expression as well.

There is a high degree of tissue specificity in the Oncostatin M induction of PA, as there is for induction of MHC antigens. When mononuclear blood cells are incubated with Oncostatin M at concentrations up to 10 ng/ml for 1 to 2 days, no change in PA activity is seen.

Other cytokines were tested for their ability to affect cell surface expression of PA activity. In contrast to the observed three-fold stimulation of cell-associated PA activity by 10 nM Oncostatin M, none of the other cytokines tested were able to stimulate this activity (FIG. 3). In fact, equimolar concentrations of TNF-α and TGF-β decreased PA activity by 56% and 95% respectively. Similarly, in a separate experiment, 13 pM interleukin-1 (IL-1) decreased PA activity by 62%.

The effect of recombinant Oncostatin M on PA activity was also measured and compared to the effect observed with the native molecule. FIGS. 4A and 4B show that recombinant Oncostatin M stimulates PA activity over the same dose range as native Oncostatin M, both preparations yielding an $ED_{50}$ of 217 pM or 6.5 ng/ml indicating identical potency.

7.2.2. Baec Cell-Surface Receptors For Oncostatin M

BAECs were analyzed for the presence of Oncostatin M cell-surface receptors as described in Section 7.1.3., supra. Competitive binding experiments were performed at near saturation conditions (FIG. 5). Analysis of Scatchard plots revealed the presence of at least two classes of cell-surface binding sites on BAECs as indicated by the curvilinear isotherm shown in FIG. 6. When analyzed by the two site model, BAECs were found to possess a total receptor concentration of 30,000 sites/cell, 495 of which correspond to a high affinity class (Kd=5.8 pM) and 29,505 of which correspond to a low affinity class (Kd=1.0 nM). Half-maximal receptor occupancy occurred at 2 ng/ml (67 pM) Oncostatin M. Maximum stimulation of PA activity (90%) required 30 ng/ml Oncostatin M, equivalent to about 80% receptor occupancy, suggesting that the low affinity/high capacity binding site may be involved in the mechanism by which Oncostatin M stimulates PA activity.

8. EXAMPLE: ANTIPROLIFERATIVE EFFECTS OF ONCOSTATIN M ON ENDOTHELIAL CELLS

The studies described herein demonstrate that Oncostatin M inhibits the serum- and bFGF-induced proliferation of endothelial cells in vitro but does not induce directional migration chemotaxis in monocytes.

8.1. Growth Inhibition Assays

Two techniques were employed for measuring the inhibition of endothelial cell growth by Oncostatin M, cell quantitation and incorporation of radiolabeled nucleotide into DNA. For the cell quantitation assay, bovine aortic endothelial cells (BAECs) were plated at low density ($1 \times 10^4$ cells/well) in 96-well tissue culture plates (Falcon) containing minimal essential media (Gibco) supplemented with 10% fetal bovine serum (Hyclone). Following a 4 hour incubation at 37 degrees C., triplicate wells were treated with increasing concentrations of Oncostatin M and incubated for an additional 72 hours. Monolayers were treated with 0.25% trypsin and the total number of cells per well was quantitated using a hemacytometer.

For measuring the incorporation of radiolabeled nucleotide into DNA, fetal bovine heart endothelial (BHE) cells (ATCC No. CRL 1395) were plated at low density ($1 \times 10^4$ cells/well) in 96-well tissue culture plates (Falcon) containing DMEM (Gibco) supplemented with 10% FBS (Hyclone). Following a 4 hour incubation at 37 degrees C., triplicate wells were treated with bFGF alone or in combination with increasing concentrations of Oncostatin M. After 48 hours incubation at 37 degrees C., wells were treated with 0.05 $\mu$Ci of 5-[$^{125}$I]-iodo-2'-deoxyuridine (Amersham) and incubated for an additional 24 hours. Monolayers were washed with PBS, fixed in 95% methanol, air-dried, and incorporated radioactivity was solubilized in 200 $\mu$l 1N NaOH. DNA synthesis was measured by quantitating the amount of radiolabeled nucleotide incorporated into the DNA of actively growing cells. After 72 hours treatment, unlabeled cells were trypsinized and counted using a hemacytometer and the results compared to the observed level of DNA synthesis.

8.2. Monocyte Chemotaxis Assay

Human peripheral blood mononuclear cells (PBMCs) were prepared from blood using Ficoll gradient separation and utilized in the chemotaxis assay. The assay was conducted in poly(vinylpyrrolidone)-free polycarbonate 8 um filters (Nucleopore Corp.; Pleasanton, Calif.) in 48-well micro chemotaxis chambers (Neuro Probe; Cabin John, Md.). Briefly, bottom chambers were filled with 55 $\mu$l PBMCs in suspension ($10^6$ cells/ml). The assembled chamber was incubated in a humidified atmosphere of 5% $CO_2$/95% air at 37 degrees C. for 3 hours. Cells that had migrated to the reverse side of the filter were fixed and stained by the Diff-Quik procedure (American Scientific Products; McGaw Park, Ill.) and five randomly chosen fields were enumerated by light microscopy at high power for cells displaying characteristic monocyte staining. Monocyte migration in response to putative chemoattractants was expressed as the mean number of monocytes per high power field (HPF), n=5. Response to the chemotactic tripeptide, fMET-Leu-Phe (Sigma; St. Louis, Mo.) was considered maximal.

8.3 Results

Angiogenesis requires that endothelial cells migrate and proliferate in response to angiogenic stimuli. Confluent cultures of BAECs respond to bFGF by increasing the saturation density of the monolayer. When grown to confluence, BAECs became density arrested at a concentration of $4-5 \times 10^5$ cells/well. Exposure to 5 ng/ml bFGF induced these cells to divide further, reaching a density of $8-10 \times 10^5$ cells/well. In order to determine whether Oncostatin M could act as an antiproliferative agent by blocking bFGF-stimulated endothelial cell growth, confluent cultures of BAECs were exposed to bFGF in the presence or absence of Oncostatin M. As shown in FIG. 7, Oncostatin M blocks the mitogenic action of bFGF in a dose-dependent manner. Cell proliferation was inhibited by low concentrations of Oncostatin M, $ED_{50}$=0.4 ng/ml or 13 pM.

The susceptibility of low density BAECs to the antiproliferative effects of Oncostatin M was assayed as described in Section 8.1., supra., as illustrated in FIG. 8. In the absence of Oncostatin M, cultures initially seeded at $1 \times 10^4$ cells/well reached a density of $8 \times 10^4$ cells/well after 72 hours incubation. In contrast, when grown in the presence of Oncostatin M, low density BAECs failed to respond to the mitogenic action of 10% serum and remained at the initial cell density ($ED_{50}$=19 pM).

Another endothelial cell line, BHE, isolated from bovine heart, which strictly requires bFGF to support its growth, was assayed for its sensitivity to Oncostatin M as described in Section 8.1., supra. FIG. 9 shows that Oncostatin M inhibits the bFGF-dependent growth of these cells in a dose-dependent manner ($ED_{50}$=16 pM). In addition to DNA labeling, cell number was determined. Cell density in the presence of bFGF alone increased from $1.8 \times 10^3$ cells/well to $3.8 \times 10^3$ cells/well, and together with Oncostatin M remained at $1 \times 10^3$ cells/well.

Certain cytokines demonstrating angiogenic properties in vivo have been shown to attract monocyte-macrophages to the site of injection. It is now believed that monocyte-macrophages induce neovascularization through the production and release of angiogenic factors (Thakral et al., 1979, J. Surg. Res. 26: 430). The ability of cytokines to stimulate chemotactic responses in monocytes may predict their ability to induce angiogenesis in vivo. Oncostatin M was evaluated for its capacity to stimulate chemotaxis using the assay described in Section 8.2., supra. The results presented in Table IV demonstrate that unlike the chemotactic activity reported for IL-1, TNF-$\alpha$ and TGF-$\beta$, Oncostatin does not induce directional migration chemotaxis in monocytes. Monocytes from a preparation of PBMCs were stimulated to migrate across a porous membrane barrier in the direction of chambers containing the potent chemoattractant fMET-Leu-Phe but, in contrast, chambers containing Oncostatin M alone had no effect on cell migration.

TABLE IV

| EFFECT OF ONCOSTATIN M ON MONOCYTE CHEMOTAXIS | |
|---|---|
| ADDITIONS TO LOWER COMPARTMENT | NUMBER of MONOCYTES/hpf |
| MEM/F-10 medium | 6 ± 3 |
| fMet—Leu—Phe, $10^{-7}$M | 83 ± 4 |
| Oncostatin M, 50 ng/ml | 6 ± 2 |

9. EXAMPLE: CHARACTERIZATION OF MORPHOLOGICL CHANGES INDUCED BY ONCOSTATIN M ON ENDOTHELIAL CELLS

The following studies characterize the morphological effects induced in bovine endothelial cells by Oncostatin M in vitro.

9.1. Cell Culture

Bovine aortic endothelial cells (BAECs) were cultured as described in Section 7.1.1., supra.

9.2. Leukocyte Adherence Assay

BAECs were grown to confluence in glass slide chambers (Lab-Tek; NUNC Inc.) in the presence of 10% fetal bovine serum. Cultures were switched to serum-free media as described in Section 7.1.1., a, treated with 1.7 nM Oncostatin M, and allowed to incubate for 24 to 48 hours. Following incubation the cell monolayers were washed three times with fresh serum-free media. Then, 250 µl serum-free media containing $5 \times 10^4$ phytohemagglutinin-activated, non-adherent leukocytes were added to the chambers and incubated for 60 minutes at 23 degrees C. to allow for cell-cell interaction (leukocytes were prepared from human peripheral blood mononuclear cells after a 72 hour incubation at 37 degrees C. on a plastic surface). Non-adhering leukocytes were removed by washing the monolayer three times with fresh serum-free media. BAECs were then fixed, stained (Diff-Quik procedure; American Scientific Products) and examined microscopically for leukocyte binding (primarily lymphoblasts). Lymphoblast binding was quantitated by averaging the number of cells observed in five randomly selected high power fields.

9.3. Oncostatin M Induces Morphological Changes In BAECs

The photomicrographs in FIGS. 10A and 10B show the morphological effects of Oncostatin M on BAECs. Oncostatin M induces alterations in BAEC monolayer architecture: the typical "cobblestone" pattern of cell alignment is lost and replaced by elongated cells with wider intercellular spacing. The observed intercellular "retraction" implies that Oncostatin M induces alterations in endothelial cell-surface properties.

The endothelial cell-surface has been shown to preferentially bind a variety of leukocytes through identified and putative intercellular adhesion molecules (Cotran and Pober, *Endothelial Cell Biology in Health and Disease;* Simonescu and Simonescu, Eds., 1988). It is known that lymphocyte adhesion is an inducible property of endothelial cells. BAECs were therefore examined for leukocyte adhesion properties following Oncostatin M treatment. The results demonstrate that Oncostatin M induces the adhesion of human leukocytes to the surface of BAEC monolayers in a time-dependent manner (FIG. 11).

To examine the mechanism by which Oncostatin M induces leukocyte adhesion, BAECs were allowed to preincubate with a monoclonal antibody (LB-2, 20 µg/ml; provided by Dr. E. A. Clark of the Regional Primate Research Center at Washington University, Seattle, Wash.) specific for Intercellular Adhesion Molecule-1 (ICAM-1) prior to Oncostatin M treatment. Preincubation with the anti-ICAM-1 MAb resulted in a 62% decrease in leukocyte adhesion suggesting that Oncostatin M induces leukocyte adhesion by upregulating the expression of heterotypic intercellular adhesion molecules such as ICAM-1. This action of Oncostatin M may extend to other leukocyte subsets in view of observations made with IL-1, IFN -gamma, TNF-α, and lipopolysaccharides, which also increase adhesion by other leukocyte subsets (Makgobe et al., 1983, Nature (London) 351: 86; Dustin and Springer, 1988, J. Cell. Biol. 107: 321).

The present invention is not to be limited by the embodiments disclosed herein which are intended as single illustrations of one aspect of the invention and any which are functionally equivalent are within the scope of the invention. Indeed, various modifications of the invention, in addition to those shown and described herein, will become apparent to those skilled in the art from the foregoing description. Such modifications are intended to fall within the scope of the appended claims.

What is claimed is:

1. A method for inhibiting endothelial tissue immunogenicity comprising treating endothelial cells that are responsive to Oncostatin M with an effective amount of Oncostatin M so that the cytokine-stimulated expression of MHC antigens on those endothelial cells is suppressed.

2. The method according to claim 1 in which the MHC antigens comprise class I HLA antigens.

3. The method according to claim 1 in which the MHC antigens comprise class II HLA antigens.

4. The method according to claim 1 in which the Oncostatin M is covalently coupled to an antibody molecule that specifically binds to a cellular antigen.

5. The method according to claim 1 in which the Oncostatin M is covalently coupled to a hormone.

6. The method according to claim 1 in which the Oncostatin M is covalently coupled to a growth factor.

7. The method according to claim 1 in which the Oncostatin M is covalently coupled to a cytokine.

8. The method according to claim 1 in which the Oncostatin M is encapsulated in a liposome.

9. The method according to claim 1 in which the Oncostatin M is encapsulated in a microcapsule.

10. The method according to claim 1 wherein the Oncostatin M is co-administered with an effective amount of TGF-β.

* * * * *